United States Patent
Wakita et al.

(10) Patent No.: US 12,060,464 B2
(45) Date of Patent: Aug. 13, 2024

(54) SILICONE RESIN-COATED SILICONE ELASTOMER PARTICLES, AND APPLICATIONS THEREOF INCLUDING ORGANIC RESIN ADDITIVES

(71) Applicant: DOW TORAY CO., LTD., Tokyo (JP)

(72) Inventors: Mari Wakita, Ichihara (JP); Hiroko Taniguchi, Ichihara (JP); Takeshi Yoshizawa, Ichihara (JP); Yasue Kanzaki, Ichihara (JP)

(73) Assignee: DOW TORAY CO., LTD., Tokyo (JP)

( * ) Notice: Subject to any disclaimer, the term of this patent is extended or adjusted under 35 U.S.C. 154(b) by 256 days.

(21) Appl. No.: 17/418,352

(22) PCT Filed: Dec. 20, 2019

(86) PCT No.: PCT/JP2019/050182
§ 371 (c)(1),
(2) Date: Sep. 28, 2021

(87) PCT Pub. No.: WO2020/137913
PCT Pub. Date: Jul. 2, 2020

(65) Prior Publication Data
US 2022/0073684 A1    Mar. 10, 2022

(30) Foreign Application Priority Data
Dec. 27, 2018  (JP) ................ 2018-244388

(51) Int. Cl.
*C08J 3/12* (2006.01)
*C08G 77/08* (2006.01)
(Continued)

(52) U.S. Cl.
CPC ............. *C08J 3/126* (2013.01); *C08G 77/08* (2013.01); *C08G 77/12* (2013.01); *C08G 77/18* (2013.01);
(Continued)

(58) Field of Classification Search
CPC ........................................ C08G 77/00–77/80
See application file for complete search history.

(56) References Cited

U.S. PATENT DOCUMENTS

| 5,538,793 A | 7/1996 | Inokuchi et al. |
| 5,756,568 A | 5/1998 | Morita et al. |

(Continued)

FOREIGN PATENT DOCUMENTS

| EP | 2216357 A1 * | 8/2010 | ............ A61K 8/891 |
| EP | 3699235 A1 | 8/2020 | |

(Continued)

OTHER PUBLICATIONS

Machine translation WO-2017191798-A1 (Year: 2023).*
(Continued)

*Primary Examiner* — Alexandre F Ferre
(74) *Attorney, Agent, or Firm* — WARNER NORCROSS + JUDD LLP

(57) ABSTRACT

Provided is a silicone resin coated silicone elastomer particle which can be easily produced on an industrial scale, has superior dispersibility and oil absorptivity in a curable organic resin such as an epoxy resin, and has superior workability due to low secondary aggregation compared to conventional silicone elastomer particles. Also provided are applications containing the particles such as organic resin additives, organic resins, coating compositions or coating agent compositions, and cosmetic compositions. The silicone resin coated silicone elastomer particles have part or all of their surface coated with a silicone resin made up of two types of siloxane units. The siloxane units are selected from D units represented by $R_2SiO_{2/2}$, T units represented by $RSiO_{3/2}$, and Q units represented by $SiO_{4/2}$. The particles
(Continued)

also have a structure in which at least two silicon atoms in the particles are cross-linked by a silalkylene group with 2 to 20 carbon atoms.

14 Claims, 1 Drawing Sheet

(51) Int. Cl.
   *C08G 77/12* (2006.01)
   *C08G 77/18* (2006.01)
   *C08G 77/20* (2006.01)
   *C08K 9/06* (2006.01)
   *C09D 7/40* (2018.01)
   *C09D 7/65* (2018.01)

(52) U.S. Cl.
   CPC ............... *C08G 77/20* (2013.01); *C08K 9/06* (2013.01); *C09D 7/65* (2018.01); *C09D 7/68* (2018.01); *C09D 7/69* (2018.01); *C09D 7/70* (2018.01); *C08G 2150/00* (2013.01)

(56) References Cited

U.S. PATENT DOCUMENTS

| | | | |
|---|---|---|---|
| 5,928,660 | A | 7/1999 | Kobayashi et al. |
| 5,945,471 | A | 8/1999 | Morita et al. |
| 5,948,469 | A | 9/1999 | Morita et al. |
| 2006/0084758 | A1* | 4/2006 | Morita .................... C08L 83/04 428/404 |
| 2009/0052017 | A1 | 2/2009 | Sasaki |
| 2010/0112023 | A1 | 5/2010 | Inokuchi et al. |
| 2010/0112074 | A1 | 5/2010 | Inokuchi et al. |
| 2010/0203095 | A1 | 8/2010 | Inokuchi et al. |
| 2010/0203097 | A1 | 8/2010 | Tanaka |
| 2011/0110994 | A1 | 5/2011 | Inokuchi et al. |
| 2011/0117146 | A1 | 5/2011 | Inokuchi et al. |
| 2012/0121909 | A1 | 5/2012 | Kobayashi et al. |
| 2013/0040144 | A1 | 2/2013 | Inokuchi et al. |
| 2013/0090448 | A1 | 4/2013 | Inokuchi et al. |
| 2013/0095324 | A1 | 4/2013 | Inokuchi et al. |
| 2014/0322280 | A1 | 10/2014 | Inokuchi |
| 2019/0038520 | A1 | 2/2019 | Igarashi |
| 2019/0144612 | A1 | 5/2019 | Hori et al. |
| 2020/0332124 | A1 | 10/2020 | Wakita et al. |

FOREIGN PATENT DOCUMENTS

| | | | |
|---|---|---|---|
| FR | 2972350 | A1 | 9/2012 |
| JP | H4348143 | A | 12/1992 |
| JP | H07196815 | A | 8/1995 |
| JP | H8109262 | A | 4/1996 |
| JP | H09208709 | A | 8/1997 |
| JP | H1036219 | A | 2/1998 |
| JP | H10175816 | | 6/1998 |
| JP | 2000063674 | A | 2/2000 |
| JP | 2003226812 | A | 8/2003 |
| JP | 2004210944 | A | 7/2004 |
| JP | 2010132877 | A | 6/2010 |
| JP | 2010132878 | A | 6/2010 |
| JP | 2010180335 | A | 8/2010 |
| JP | 2011026469 | A | 2/2011 |
| JP | 2011102354 | A | 5/2011 |
| JP | 2011105663 | A | 6/2011 |
| JP | 2011168634 | A | 9/2011 |
| JP | 2011219547 | A | 11/2011 |
| JP | 2012517959 | A | 8/2012 |
| JP | 2013040241 | A | 2/2013 |
| JP | 2013087141 | A | 5/2013 |
| JP | 2014214263 | A | 11/2014 |
| WO | 2006098334 | A1 | 9/2006 |
| WO | 2007061032 | A1 | 5/2007 |
| WO | 2011002695 | A1 | 1/2011 |
| WO | 2017142068 | A1 | 8/2017 |
| WO | 2017191798 | A1 | 11/2017 |
| WO | WO-2017191798 | A1 * | 11/2017 ............. A61K 8/891 |
| WO | 2019124418 | A1 | 6/2019 |

OTHER PUBLICATIONS

"Silicones", Apr. 15, 2003 (Apr. 15, 2003), Encyclopedia of Polymer Science and Technology, Wiley, US, pp. 765-841, XP007918236.
Machine assisted English translation of WO2007061032A1 obtained from https://patents.google.com/patent on May 2, 2022, 9 pages.
English translation of the International Search Report for PCT/JP2019/050182 dated Mar. 10, 2020, 3 pages.
Machine assisted English translation of JP2000063674A obtained from https://patents.google.com/patent on Sep. 29, 2021, 9 pages.
Machine assisted English translation of JP2011219547A obtained from https://patents.google.com/patent on Sep. 29, 2021, 10 pages.
Machine assisted English translation of JP2011168634A obtained from https://patents.google.com/patent on Sep. 29, 2021, 9 pages.
Machine assisted English translation of JP2003226812A obtained from https://patents.google.com/patent on Sep. 29, 2021, 13 pages.
English translation of International Search Report for PCT/JP2018/046703 dated Mar. 12, 2019, 2 pages.
Machine assisted English translation of JPH08109262A obtained from https://patents.google.com/patent on Sep. 17, 2020, 17 pages.
Machine assisted English translation of JPH09208709A obtained from https://patents.google.com/patent on Sep. 17, 2020, 10 pages.
Machine assisted English translation of JPH1036219A obtained from https://patents.google.com/patent on Sep. 17, 2020, 11 pages.
Machine assisted English translation of FR2972350A1 obtained from https://patents.google.com/patent on Aug. 18, 2021, 8 pages.

* cited by examiner

SILICONE RESIN-COATED SILICONE ELASTOMER PARTICLES, AND APPLICATIONS THEREOF INCLUDING ORGANIC RESIN ADDITIVES

CROSS-REFERENCE TO RELATED APPLICATIONS

This application is the National Stage of International Appl. No. PCT/JP2019/050182 filed on 20 Dec. 2019, which claims priority to and all advantages of Japanese Patent Application No. 2018-244388 filed on 27 Dec. 2018, the content of which is hereby incorporated by reference.

TECHNICAL FIELD

The present invention relates to silicone resin coated silicone elastomer particles having superior dispersibility in organic resins such as epoxy resins, having a smooth surface coated with a silicone resin, having a small secondary agglomerate particle diameter, not readily agglomerating, and having superior workability as cosmetic raw material. Furthermore, the present invention relates to cosmetic raw materials, cosmetic compositions, organic resin additives and other applications including these oil-containing silicone elastomer particles.

BACKGROUND ART

Silicone elastomer particles are used as modifying additives in cosmetics, paints, inks, thermosetting organic resins, thermoplastic organic resins, and the like. They are particularly suitable as internal stress relief agents for thermosetting organic resins and surface lubricants for organic resin films. In particular, the silicone elastomer particles have superior heat resistance and flexibility derived from the elastomer framework, making them particularly suitable as internal stress relief agents in high-performance organic resins, especially in resin substrates for semiconductors, functional organic resin films, and resin coatings thereon.

On the other hand, silicone elastomer particles are easily charged, and when added to the thermosetting organic resin described above, they tend to aggregate and have poor uniformity of dispersion in the resin, which may result in insufficient performance anticipated as a stress relief agent for the organic resin after curing. For this reason, Patent Documents 1 to 4 (in particular, Patent Document 3) propose a silicone composite particle in which the silicone particle surface is coated with a silicone resin made up of silsesquioxane units represented by $SiO_{3/2}$, and in which dispersibility, and the like in organic resins is improved, and propose applications such as internal stress relief agents and cosmetic compositions thereof. However, these silicone composite particles have improved dispersibility and stress relief properties in organic resins compared to silicone elastomer particles blended alone, but because the surface thereof is coated with a silicone resin structure made up of silsesquioxane units, they tend to scatter and adhere to containers (including inner bags made of organic resins such as vinyl), worsening workability. In addition, there is still room for improvement in oil absorption thereof and other properties, and there is a need for further improvement in its texture as a cosmetic raw material.

On the other hand, as silicone particles having superior dispersibility, high lipophilicity, and high storage stability, the present applicant proposes a silicone particle containing an alkenyl group with a carbon number of 4 to 20, which is made by curing a crosslinkable composition for forming silicone particles having a low content of silicon-bonded hydrogen atoms per unit mass and containing an alkenyl group having 4 to 20 carbon atoms, such as a hexenyl group, as described in Patent Document 5. However, although these silicone particles have the advantages of sufficient dispersibility and lipophilicity as cosmetic raw materials, there is still room for improvement in their dispersibility in organic resins, their oil absorption properties, and their performance as cosmetic raw materials with superior usability.

Furthermore, in Patent Documents 6 to Patent Document 8, the present applicant has proposed core-shell type crosslinked silicone particles, and the like, in which the surface of the crosslinked silicone particles are coated with a silicone compound (siloxane, silane, and the like) having a silicon-bonded hydrolyzable group. However, even the silicone resin coated crosslinked silicone particles described in these documents could not sufficiently solve the problems originating from the agglomeration of primary particles described above, and there was still room for improvement in their performance and industrial production efficiency.

RELATED ART DOCUMENTS

Patent Documents

Patent Document 1: Japanese Unexamined Patent Application Publication No. 2010-132878
Patent Document 2: Japanese Unexamined Patent Application Publication No. 2011-105663
Patent Document 3: Japanese Unexamined Patent Application Publication No. 2011-168634
Patent Document 4: Japanese Unexamined Patent Application Publication No. 2011-102354
Patent Document 5: International Patent Application (WO) 2017/191798
Patent Document 6: Japanese Unexamined Patent Application Publication No. 2003-226812
Patent Document 7: PCT International Publication No. 2006/098334
Patent Document 8: International Patent Application PCT/JP2018/46703

SUMMARY OF THE INVENTION

Figure 1:
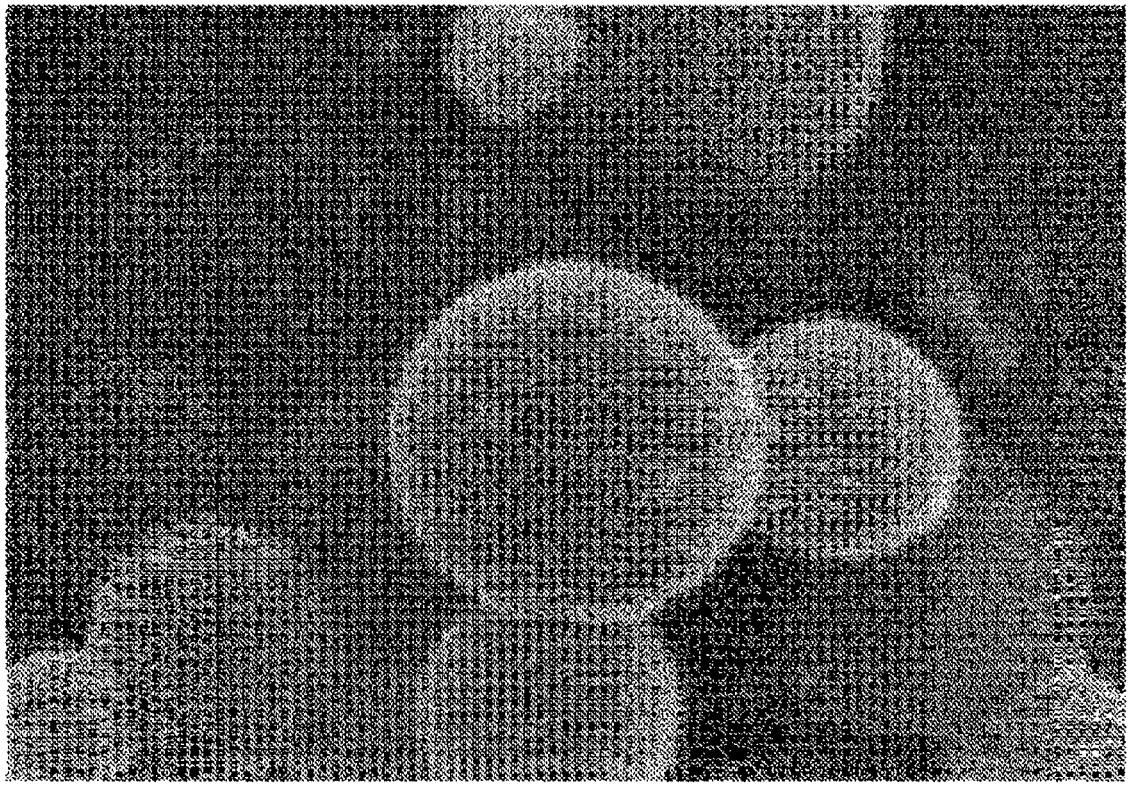
FIG. 1 is an electron photomicrograph of silicone resin coated silicone elastomer particles of Example 1

Problem to be Solved by the Invention

An object of the present invention is to provide silicone resin coated silicone elastomer particles which can be easily produced on an industrial scale, have superior dispersibility and oil absorptivity in curable organic resins such as epoxy resins, and have superior workability due to lower secondary aggregation than conventional silicone elastomer particles. Further, an additional object of the present invention is to provide organic resin additives, cosmetic raw materials, and other applications for said silicone resin coated silicone elastomer particles.

Means for Solving the Problem

In order to solve the problem described above, as a result of intensive investigation, the inventors have discovered that the problems described above can be resolved using a silicone resin coated silicone elastomer particle in which part or all of the surface thereof is coated with a silicone resin (in other words DQ, DT, or TQ silicone resin) made up of two types of siloxane units selected from D siloxane units represented by $R_2SiO_{2/2}$ (R is a monovalent organic group), T siloxane units represented by $RSiO_{3/2}$ (R is a monovalent organic group), and Q siloxane units represented by $SiO_{4/2}$, suitably with DQ silicone resin, and has a structure in which at least two silicone atoms in the silicone elastomer particle are crosslinked by a silalkylene group having 2 to 20 carbons and achieved the present invention. The silicone resin coated silicone elastomer particles are easily obtained by a manufacturing method that includes a process in which a mixture containing a crosslinkable silicone component and hydrolyzable silanes are emulsified in water and crosslinked, and simultaneously/subsequently with the crosslinking reaction, the surface of the mixture is coated with a silicone resin that is a condensation product of the hydrolyzable silanes and thus has superior industrial manufacturability.

The inventors have also found that the silicone resin coated silicone elastomer particles described above can be used for an organic resin additive, a cosmetic raw material and other applications, and that the problems described above can be solved by organic resins and the like containing the same.

In other words, an object of the present invention is achieved by:

[1] Silicone resin coated silicone elastomer particles coated with one or more silicone resins selected from:
   (i) a DQ silicone resin made up of a D siloxane unit represented by $R_2SiO_{2/2}$ (R is a monovalent organic group) and a Q siloxane unit represented by $SiO_{4/2}$;
   (ii) a DT silicone resin made up of a D siloxane unit represented by $R_2SiO_{2/2}$ (R is a monovalent organic group) and a T siloxane unit represented by $RSiO_{3/2}$ (R is a monovalent organic group); and
   (iii) TQ silicone resin made up of a T siloxane unit represented by $RSiO_{3/2}$ (R is a monovalent organic group) and a Q siloxane unit represented by $SiO_{4/2}$, and
   having a structure in which at least two silicon atoms in the silicone elastomer particles are cross-linked by a silalkylene group with a carbon number of 2 to 20.

Suitably, the object of the present invention is achieved by silicone resin coated silicone elastomer particles having the following structure.

[2] The silicone resin coated silicone elastomer particles in [1] where the silicone resin coating amount is in the range of 5.0 to 40.0 mass parts for 100 mass parts of the silicone elastomer particles.

[3] A silicone resin coated silicone elastomer particle according to [1] or [2], wherein the silicone resin comprises D-siloxane units represented by $R^1_2SiO_{2/2}$ (where $R^1$ is an alkyl group having 1 to 20 carbon atoms or an aryl group having 6 to 20 carbon atoms), and a Q-siloxane unit represented by $SiO_{4/2}$, and the weight ratio thereof is a DQ silicone resin in the range of 8:2 to 3:7.

[4] The silicone resin coated silicone elastomer particle according to any one of [1] to [3], wherein the average primary particle diameter as measured by a laser diffraction scattering method is 0.5 to 20 μm.

[5] The silicone resin coated silicone elastomer particle according to any one of [1] to [4], wherein the silicone elastomer particle in a state not coated with a silicone resin has a JIS-A hardness, as measured by curing the pre-cure crosslinkable composition for forming the silicone elastomer particle in sheet form, in the range of 10 to 80.

[6] The silicone resin coated silicone elastomer particle according to any one of [1] to [5], wherein the silicone resin on the surface of the silicone elastomer particle is a silicone resin including only a condensation reaction product of two or more types selected from diorganodialkoxysilane, organotrialkoxysilane, and tetraalkoxysilane.

[7] The silicone resin coated silicone elastomer particle according to any one of [1] to [6], wherein the silicone resin on the surface of the silicone elastomer particle is a DQ silicone resin including only a condensation reaction product of diorganodialkoxysilane and tetraalkoxysilane and having a weight ratio of 8:2 to 3:7.

[8] The silicone resin coated silicone elastomer particle according to any one of [1] to [7], wherein the content of silicon-bonded hydrogen per unit mass is 300 ppm or less.

[9] The silicone resin coated silicone elastomer particle according to any one of [1] to [8], and the silicone elastomer particles in a state not coated with a silicone resin and the crosslinkable composition for forming silicone elastomer particles prior to curing is a crosslinkable composition including:
   (a) an organopolysiloxane having at least two alkenyl groups with 2 to 20 carbon atoms in the molecule;
   (b) an organohydrogenpolysiloxane having at least two silicon-bonded hydrogen atoms in the molecule; and
   (c) a hydrosilylation reaction catalyst; wherein
   the molar ratio of the alkenyl group content (Alk) of component (a) to the silicon-bonded hydrogen atom content (H) of component (b) is in the range of H/Alk=0.7 to 1.5.

The object of the present invention is also achieved by compositions containing the silicone resin coated silicone elastomer particles described above or by their use in specific applications. Specific examples are as follows.

[10] An organic resin additive made up of the silicone resin coated silicone elastomer particle according to any one of [1] to [9].

[11] An organic resin made up of the silicone resin coated silicone elastomer particle according to any one of [1] to [9].

[12] A curable organic resin composition made up of the silicone resin coated silicone elastomer particle according to any one of [1] to [9].

[13] A paint composition or coating composition made up of the silicone resin coated silicone elastomer particle according to any one of [1] to [9].

[14] A cosmetic composition made up of the silicone resin coated silicone elastomer particle according to any one of [1] to [9].

Effects of the Invention

The silicone resin coated silicone elastomer particles of the present invention can be easily produced on an industrial scale, have excellent dispersibility and oil absorptivity in curable organic resins such as epoxy resins, and have superior workability because they have less secondary aggregation than conventional silicone elastomer particles and can be suitably used in organic resin additives with superior function such as stress relief properties, cosmetic raw materials with superior feel and the like, and other applications. Furthermore, a cosmetic composition containing the silicone resin coated silicone elastomer particles of the present invention can provide cosmetics with an excellent sensation during use.

PREFERRED MODE FOR CARRYING OUT THE INVENTION

The silicone resin coated silicone elastomer particles of the present invention, in particular applications thereof including organic resin additives, organic resins containing the same, paints and coatings, and cosmetic compositions, will be described in detail below.

The silicone resin coated silicone elastomer particles of the present invention have part or all of their surface coated with a silicone resin (in other words DQ, DT and TQ silicone resins) made up of two types of siloxane units selected from D siloxane units represented by $R_2SiO_{2/2}$ (R is a monovalent organic group), T siloxane units represented by $RSiO_{3/2}$ (R is a monovalent organic group) and Q siloxane units represented by $SiO_{4/2}$ and have a structure in which at least two silicon atoms in the silicone elastomer particles are cross-linked by a silalkylene group with 2 to 20 carbon atoms. In the following, the term "silicone elastomer particles" simply refers to silicone elastomer particles before they are coated or compounded with a silicone resin.

[Silicone Elastomer Particles Before Coating]
First, silicone elastomer particles have a structure in which at least two silicon atoms are cross-linked within the particle by a silalkylene group with a carbon number of 2 to 20. The silalkylene cross-linked structure is preferably formed by a progressive hydrosilylation reaction of an alkenyl group with a carbon number of 2 to 20 and a silicon-bonded hydrogen atom between different siloxane molecules. In the present invention, the silalkylene group which cross-links between the silicon atoms in the siloxane constituting the silicone elastomer particles and other silicon atoms is preferably a silalkylene group having a carbon number of 2 to 16, and a carbon number in the range of 2 to 8 is more preferable, and an ethylene group, a propylene group, a butylene group or a hexylene group are particularly preferred.

Here, unlike the silicone resin coated silicone elastomer particles proposed by the applicants in Patent Document 8, the present invention employs a coating with a specific silicone resin as described below, so that even if a silalkylene group having three or fewer carbon atoms, which is introduced by a hydrosilylation reaction such as by a vinyl group, exists in the particle, there is an advantage that the technical effect of the present invention is fully realized.

The silicone elastomer particles according to the present invention are not particularly limited in terms of the average primary particle diameter before being coated with the silicone resin, but in the case of an organic resin additive added for the purpose of stress relief of the organic resin, the average primary particle diameter measured using a laser diffraction scattering method is preferably 0.4 to 19 μm. Such silicone elastomer particles are further coated on the surface with a silicone resin made up of siloxane units represented by $SiO_{4/2}$, and are further classified as necessary to eventually provide silicone resin coated silicone elastomer particles having an average primary particle diameter of 0.5 to 20 μm as measured by laser diffraction scattering. It goes without saying that after coating, the average primary particle diameter of the particles increases compared to the silicone elastomer particles before coating.

The shape of the silicone elastomer particles of the present invention includes, for example, spherical, regular spherical shape, elliptical, and irregular shapes, and in particular, spherical and regular spherical shapes are preferred. Note, in the present invention, an aqueous suspension containing spherical silicone elastomer particles coated with silicone resin can be obtained in a single reaction vessel by emulsifying hydrolyzable silanes with crosslink reactive silicone raw materials, and then drying the aqueous suspension using a vacuum dryer, hot air circulation oven, or a spray dryer, enabling direct manufacture of spherical silicone resin coated silicone elastomer particles so it is not necessarily necessary to separately produce uncoated silicone elastomer particles and coat the surface thereof.

The silicone elastomer particles of the present invention are elastomer particles having elasticity from the viewpoint of technical effects such as a feeling of use as a cosmetic raw material, stress relief when blended with an organic resin, and prevention of stickiness, and the like, suitably, with the crosslinkable composition for forming the silicone elastomer particles before curing thereof in a sheet form when cured, the hardness is preferably in the range of 10 to 80 as measured by a JISA hardness tester as specified in JIS K6301. If the JIS-A hardness of the rubber sheet measured by curing the crosslinkable composition for forming silicone elastomer particles into a sheet form is within the above range, the resulting silicone elastomer particles will have sufficiently low aggregation and will tend to have exceptional flowability, dispersibility, smoothness, and softness. Furthermore, by selecting the JIS-A hardness described above, stress relief properties can be improved when blended with organic resin, and the workability after silicone resin coating is also excellent. Furthermore, the particles after silicone resin coating can improve the sensation during use of cosmetic compositions containing the particles. When the silicone resin coated silicone elastomer particles of the present invention are used as a stress relief agent for organic resins, it is preferable to use silicone elastomer particles having a JIS-A hardness in the range of 30 to 80, and particularly preferably in a range of 50 to 80, as described above.

The silicone elastomer particles according to the present invention may further contain 300 ppm or less of silicon-bonded hydrogen per unit mass. The content of the silicon-bonded hydrogen is further desirably 250 ppm or less, and more desirably 200 ppm or less. Further, more desirably 150 ppm or less, more desirably 100 ppm or less, more desirably 50 ppm or less, and even more desirably 20 ppm or less. With the silicone elastomer particles according to the present invention, if the amount of silicon-bonded hydrogen becomes large, crosslinking reaction proceeds with reactive functional groups remaining in other silicone elastomer particles, causing aggregation of the silicone elastomer particles or silicone resin coated silicone elastomer particles over time. Furthermore, by reducing the silicon-bonded hydrogen in the silicone elastomer particles in the present invention, the generation of flammable hydrogen gas over time when these particles are stored is suppressed, and the resulting silicone resin coated silicone elastomer particles are not subject to problems such as container expansion or ignition and this is advantageous regarding safe handling for organic resin additives and other applications.

A typical method for measuring the silicon-bonded hydrogen in silicone elastomer particles is to use gas chromatography (headspace method) in contact with alkali. For example, an ethanol solution of potassium hydroxide at a concentration of 40%, which is equal to the unit mass, is added to the silicone elastomer particles and allowed to stand for 1 hour, and the hydrogen gas generated by the endpoint of the reaction is collected and quantified using headspace gas chromatography. The details are disclosed, for example, in Patent Document 5 described above.

[Crosslinkable Composition for Forming Silicone Elastomer Particles]
The silicone elastomer particles described above have a structure in which at least two silicon atoms in the molecule are crosslinked by silalkylene groups with 4 to 20 carbon atoms, and can be obtained by curing a crosslinkable composition containing the following components by a hydrosilylation reaction.

(a) an organopolysiloxane having at least two alkenyl groups with 2 to 20 carbon atoms in the molecule;
(b) an organohydrogenpolysiloxane having at least two silicon-bonded hydrogen atoms in the molecule; and
(c) a hydrosilylation reaction catalyst Component (a) is an organopolysiloxane having at least two alkenyl groups with 2 to 20 carbon atoms in the molecule, the structure of which is not particularly limited and may be one or more type of structure selected from a linear, cyclic, reticulate, or partially branched linear structure, and a straight-chain organopolysiloxane is particularly preferred. The viscosity of component (a) should be in a viscosity range that enables the crosslinkable composition described above to be dispersed in water or with a spray dryer or the like. Specifically, it is preferable to be in the range of 20 to 100,000 mPa·s at 25° C. In particular, it is preferable to be in the range of 20 to 10,000 mPa·s.

From the viewpoint of oil absorption and dispersibility of the silicone elastomer particles, component (a) is preferably a straight-chain organopolysiloxane in which the content of the dimethyl siloxane units represented by the formula: $(CH_3)_2SiO$ is 90 mol % or more of all siloxane units other than the siloxane units at the molecular terminals. Similarly, from the viewpoint of improving the oil absorptivity of the resulting silicone elastomer particles and contact failure of electronic components or the like equipped with resin components after blending, cyclic or chain-like organopolysiloxane of low degree of polymerization (degree of polymerization 3 to 20) is preferably removed from component (a) beforehand by stripping or the like.

Examples of the alkenyl group having a carbon number of 2 to 20 in component (a) include a vinyl group, an allyl group, a butenyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, a octadecenyl group, a nonadecenyl group, and a icosenyl group. From the viewpoint of reactivity and aggregation, the number of carbon atoms of the alkenyl group is in the range of 2 to 16, preferably in the range of 2 to 8, and the use of a vinyl group or a hexenyl group is particularly preferable. The alkenyl group is preferably located at the molecular chain terminal of the organopolysiloxane, but it may also be located on a side chain or on both.

Examples of the groups bonded to the silicon atom other than the alkenyl group include alkyl groups such as methyl, ethyl, propyl, and butyl groups; cycloalkyl groups such as cyclopentyl and cyclohexyl groups; aryl groups such as phenyl, tolyl, and xylyl groups; aralkyl groups such as benzyl, phenethyl, and 3-phenylpropyl group; or a non-substituted or substituted monovalent hydrocarbon group such as a halogenated alkyl group such as a 3-chloropropyl group or a 3,3,3-trifluoropropyl group. Suitably, component (a) is preferably a straight-chain organopolysiloxane represented by the following chemical formula (1).

[Formula 1]

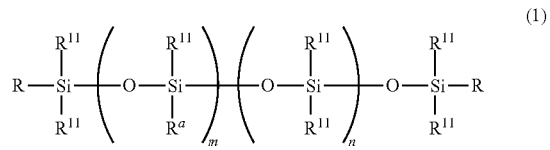

In Formula (1), each $R^{11}$ is independently an unsubstituted or halogen atom-substituted alkyl group (for example, a methyl group, or the like) having 1 to 20 carbon atoms, an aryl group (for example, a phenyl group, or the like) having 6 to 22 carbon atoms, or a hydroxyl group, and a methyl group or a phenyl group is preferable from an industrial point of view. $R^a$ is an alkenyl group having 2 to 20 carbon atoms, and is particularly preferably a vinyl group or a hexenyl group. R is a group represented by $R^{11}$ or $R^a$. m is a number greater than or equal to 0, and n is a number greater than or equal to 1. However, m, n, and R are numbers such that the content of the vinyl ($CH_2=CH-$) portion of the alkenyl group having 2 to 12 carbon atoms in the organopolysiloxane molecule represented by formula (1) above is 0.5 to 3.0 mass %, and the viscosity of component (a) is 20 to 10,000 mPa·s at 25° C.

Component (a) may be organopolysiloxane having hexenyl groups at both terminals as well as side chains of the molecular chain, represented by the following structural formula (2), and may be an organopolysiloxane in which some or all of the hexenyl groups of the structural formula (2) are vinyl groups.

[Formula 2]

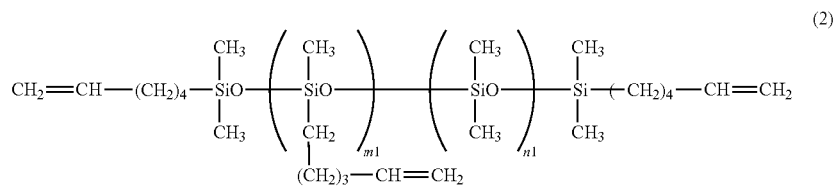

(In Formula (2), m1 is a number greater than or equal to 0, n1 is a positive number, and m1 is a number at which the content of the vinyl ($CH_2=CH-$) portion in the hexenyl group $(CH_2)_4CH=CH_2$) in the molecule represented by Formula (2) is in the range of 0.5 to 3.0 mass %, more preferably in the range of 1.0 to 2.0 mass %. Also, m1+n1 is a number within a range wherein the viscosity at 25° C. of the organopolysiloxane represented by Formula (2) is 20 mPa·s or more, and more suitably, between 100 to 500 mPa·s).

Component (a) may be a branched organopolysiloxane having an alkenyl group at the end of the molecular chain, represented by $(R^a R^{11}{}_2 SiO)_4 Si$. In the formula, $R^a$ is an alkenyl group having 2 to 20 carbon atoms, and each $R^{11}$ is an independent unsubstituted or halogen atom-substituted alkyl group (for example, methyl group, and the like) having 1 to 20 carbon atoms, an aryl group (for example, phenyl group, and the like) having 6 to 22 carbon atoms, or a hydroxyl group. More specifically, component (a) may be a branched organopolysiloxane represented by $(ViMe_2SiO)_4Si$, $(HexMe_2SiO)_4Si$, in which Vi represents a vinyl group, Me represents a methyl group, and Hex represents a hexenyl group.

(b) An organohydrogen polysiloxane having at least two silicon-bonded hydrogen atoms in the molecule is a crosslinking agent of component (a), and it is preferable to have at least three silicon-bonded hydrogen atoms in one molecule, and the bonding positions of the hydrogen atoms in the molecule are not particularly limited.

Examples of an organic group other than a hydrogen atom that is bonded to a silicon atom contained by component (b), include an alkyl group such as a methyl group, an ethyl group, a propyl group, a butyl group, or an octyl group, and a methyl group is preferable. Examples of the molecular structure of the organohydrogen polysiloxane of component (b), include straight-chain, branched-chain, and branched-cyclic, or a combination of one or more thereof. The number of silicon-bonded hydrogen atoms in a molecule is the average value of all molecules.

The viscosity of component (b) at 25° C. is 1 to 1,000 mPa-s, preferably 5 to 500 mPa-s. This is because if the viscosity of component (b) at 25° C. is less than 1 mPa-s, component (b) is easily volatilized from the crosslinkable composition containing it, and if the viscosity exceeds 1,000 mPa-s, the curing time of the crosslinkable composition containing such component (b) may become longer or may cause curing failure. Such component (b) is not particularly limited, and examples include, dimethylsiloxane-methylhydrogensiloxane copolymer capped at both molecular terminals with trimethylsiloxy groups, dimethylsiloxane-methylhydrogensiloxane copolymer capped at both molecular terminals with dimethylhydrogensiloxy groups, dimethylpolysiloxane capped at both molecular terminals with dimethylhydrogensiloxy groups, methylhydrogenpolysiloxane capped at both molecular terminals with trimethylsiloxy groups, cyclic methylhydrogenpolysiloxane, and cyclic methylhydrogensiloxane-dimethylsiloxane copolymer.

Here, the value of H/Alk, which is the molar ratio (=reaction ratio in the hydrosilylation reaction) of the alkenyl group content (Alk) of component (a) to the silicon-bonded hydrogen atom content (H) of component (b), is preferably in the range of 0.7 to 1.5. The lower limit of said H/Alk is preferably 0.80 or more, 0.85 or more, 0.90 or more, 0.95 or more, and the upper limit is 1.50 or less, and preferably, 1.30 or less. If the upper limit of H/Alk exceeds the aforementioned value, unreacted silicon-bonded hydrogen atoms tend to remain after the reaction; conversely, if the upper limit of H/Alk is less than the aforementioned value, unreacted alkenyl groups tend to remain after the reaction. Since these are curing reactive groups, if a large amount of them remain in the particles, they may cause crosslinking reactions between particles over time, resulting in aggregation and poor dispersion of the resulting silicone elastomer particles or silicone resin coated silicone elastomer particles, and if reactive hydrogen atoms remain, they may cause the generation of flammable hydrogen gas over time. Particularly suitably, when the value of H/Alk is in the range of 0.9 to 1.30, the curing reactive groups are completely consumed and the crosslinking reaction is terminated, and the aggregation over time between particles can be effectively suppressed.

Component (c) is a hydrosilylation reaction catalyst, and is a catalyst which promotes an addition reaction (hydrosilylation reaction) between a silicon-bonded alkenyl group present in the crosslinkable composition described above and a silicon-bonded hydrogen atom. Examples of preferred hydrosilylation reaction catalysts are hydrosilylation reaction catalysts containing platinum metal, such as platinic acid chloride, alcohol-modified platinic acid chloride, olefin complexes of platinic acid chloride, complexes of platinic acid chloride with ketones, complexes of platinic acid chloride with vinyl siloxane, platinum tetrachloride, platinum fine powder, platinum supported on an alumina or silica carrier, platinum black, olefin complexes of platinum, alkenylsiloxane complexes of platinum, carbonyl complexes of platinum, and thermoplastic organic resin powders such as methyl methacrylate resin, polycarbonate resin, polystyrene resin, and silicone resin containing these platinum-based catalysts. In particular, platinum alkenylsiloxane complexes such as a complex of platinum chloride with divinyltetramethyldisiloxane, a complex of platinum chloride with tetramethyltetravinylcyclotetrasiloxane, a platinum divinyltetramethyldisiloxane complex, and a platinum tetramethyltetravinylcyclotetrasiloxane complex can be preferably used. Note, as the catalyst for promoting the hydrosilylation reaction, a non-platinum based metal catalyst such as iron, ruthenium, iron/cobalt, or the like may be used.

The amount of component (c) added to the crosslinkable composition should be a catalytic quantity, and usually, an amount in which the amount of the platinum-based metal contained by component (c) is in the range of 1 to 1,000 ppm relative to the total mass of the crosslinkable composition described above is preferred, and an amount in the range of 5 to 500 ppm is even more preferred. The amount of platinum metal in the silicone elastomer particles may be reduced by the method proposed by the present inventors in Japanese Unexamined Patent Application 2014-122316.

The timing of adding component (c) to the crosslinkable composition can be selected according to the method of forming the silicone elastomer particles, and may be in the form of adding to the composition in advance, or in the form of feeding component (a) or component (b) from different spray lines and adding component (c) to one of them and mixing during spraying. Similarly, when the silicone elastomer particles are formed via aqueous suspension via emulsification into water, they may be added beforehand to the crosslinkable composition, or a separate emulsion containing component (c) may be added to the water.

The crosslinkable composition described above may include a curing retarder represented by a hydrosilylation reaction inhibitor. Examples of such curing retarders are acetylene compounds, enyne compounds, organic nitrogen compounds, organic phosphorus compounds, and oxime compounds. Specific compounds include 2-methyl-3-butyn-2-ol, 3,5-dimethyl-1-hexin-3-ol, 3-methyl-1-pentin-3-ol, 2-phenyl-3-butyn-2-ol, and 1-ethynyl-1-cyclohexanol (ETCH) and other alkyne alcohols; 3-methyl-3-trimethylsiloxy-1-butyn, 3-methyl-3-trimethylsiloxy-1-butyn, 3-methyl-3-trimethylsiloxy-1-pentyn, 3,5-dimethyl-3-trimethylsiloxy-1-hexine, 3-methyl-3-penten-1-yne, and 3,5-dimethyl-3-hexene-1-yne enyne compounds; 1-ethynyl-1-trimethylsiloxycyclohexane, bis(2,2-dimethyl-3-butynoxy) dimethylsilane, methyl(tris(1,1-dimethyl-2-propynyloxy)) silane, 1,3,5,7-tetramethyl-1,3,5,7-tetravinylcyclotetrasiloxane, and alkenylsiloxane such as 1,3,5,7-tetramethyl-1,3,5,7-tetrahexenylcyclotetrasiloxane and the like. The amount added is within the range of 0.001 to 5 mass parts per 100 mass parts of component (a), but can be designed as appropriate depending on the type of curing retarder used, the characteristics of the hydrosilylation reaction catalyst used, and the amount used.

The crosslinkable composition may include components other than the above components to the extent that the technical effects of the present invention are not impaired.

For example, aliphatic hydrocarbons such as n-hexane, cyclohexane and n-heptane; aromatic hydrocarbons such as toluene, xylene and mecitylene; ethers such as tetrahydrofuran and dipropyl ether; silicones such as hexamethyldisiloxane, octamethyltrisiloxane, decamethyltetrasiloxane; esters such as ethyl acetate, butyl acetate and propylene glycol monomethyl ether; organic solvents such as acetone, and ketones such as methyl ethyl ketone and methyl isobutyl ketone; polydimethylsiloxane or polydimethyldiphenylsiloxane and other non-reactive organopolysiloxane (including chain or cyclic organopolysiloxane with low viscosity of about 0.5 to 10 mPas at 25° C.); phenol-based, quinone-based, amine-based, phosphorus-based, phosphite, sulfur or thioether based and other antioxidants; light stabilizers such as triazole or benzophenone type; flame retardants such as phosphate ester type, halogen type, phosphorus type or antimony type; one or more types of antistatic agents including cationic surfactants, anionic surfactants, nonionic surfactants and the like; dyes; pigments and the like can be included.

[Coating with Silicone Resin]

The silicone resin coated silicone elastomer particles of the present invention are characterized in that part or all of the surface of the silicone elastomer particles is coated with a silicone resin (in other words, DQ, DT and TQ silicone resins) made up of two types of siloxane units selected from D siloxane units represented by $R_2SiO_{2/2}$ (R is a monovalent organic group), T siloxane units represented by $RSiO_{3/2}$ (R is a monovalent organic group) and Q siloxane units represented by $SiO_{4/2}$, suitably with a DQ silicone resin.

Specifically, the silicone resin used for such coating is one or more silicone resins selected from:
(i) a DQ silicone resin made up of a D siloxane unit represented by $R_2SiO_{2/2}$ (R is a monovalent organic group) and a Q siloxane unit represented by $SiO_{4/2}$;
(ii) a DT silicone resin made up of a D siloxane unit represented by $R_2SiO_{2/2}$ (R is a monovalent organic group) and a T siloxane unit represented by $RSiO_{3/2}$ (R is a monovalent organic group); or
(iii) a TQ silicone resin made up of a T siloxane unit represented by $RSiO_{3/2}$ (R is a monovalent organic group) and a Q siloxane unit represented by $SiO_{4/2}$, and
the silicone resins other than the above are preferably less than 5 mass %, less than 3 mass %, and in particular preferably less than 1 mass % of the total silicone resin used to coat the silicone elastomer particles.

Most suitably, other components providing silicone resin are not intentionally added to the surface of the silicone elastomer particles, and it is most preferable to have no other silicone resin at all. If other silicone resins (for example, silsesquioxane resin represented by $RSiO_{3/2}$) are included, the resulting silicone resin coated silicone elastomer particles may tend to scatter or adhere to the container during handling, or the problem of agglomeration may not be sufficiently resolved, resulting in deterioration of workability and work efficiency.

In the present invention, by selectively using two types of siloxane units selected from different siloxane units, D, T and Q, the surface of the silicone elastomer particles can be smoothly coated, and in particular, secondary aggregation between the particles can be effectively suppressed, thereby improving dispersibility, workability and compounding stability.

In the present invention, suitably, the silicone resin is a DQ silicone resin, with D siloxane units represented by $R^1_2SiO_{2/2}$ ($R^1$ is an alkyl group having 1 to 20 carbon atoms or an aryl group having 6 to 20 carbon atoms) and Q siloxane units represented by $SiO_{4/2}$, and a DQ silicone resin having a weight ratio thereof in the range of 8:2 to 3:7 is particularly preferable, and a DQ silicone resin having a weight ratio thereof in the range of 7:3 to 5:5 is most preferable. The D units that make up the silicone resin form 2 siloxane bonds, forming a linear siloxane bond, while the Q units form 4 siloxane bonds, forming a highly branched network or reticulated siloxane bond. Therefore, when the amount of D units is in said range, a large amount of a moderately flexible polydiorganosiloxane structure is contained in the silicone resin, and the smoothness, flexibility, and followability of the silicone resin film on the surface of the silicone elastomer particles are improved, and in particular the formation of secondary agglomerated particles is effectively suppressed.

The silicone resins described above can be obtained by hydrolysis reactions or dehydration/de-alcohol condensation reactions of the silane compounds that provide these siloxane units on the surface of the silicone elastomer particles.

More specifically, the silicone resins described above can be obtained through a condensation reaction of a mixture of two or more hydrolyzable silanes selected from hydrolyzable silanes represented by $R_2Si(OA)_2$ (in which R is a monovalent organic group and A is independently a hydrogen atom, an alkyl group having 1 to 6 carbon atoms, or a phenyl group), $RSi(OA)_3$ (in which R is a monovalent organic group and A is independently a hydrogen atom, an alkyl group having 1 to 6 carbon atoms, or a phenyl group), and hydrolyzable silanes represented by $Si(OA)_4$ (in which A is independently a hydrogen atom, an alkyl group having 1 to 6 carbon atoms, or a phenyl group).

In the formula, R is a monovalent organic group and examples include alkyl groups such as methyl, ethyl, propyl and butyl groups; cycloalkyl groups such as cyclopentyl and cyclohexyl groups; vinyl, allyl, butenyl, pentenyl, hexenyl, heptenyl, octenyl, nonenyl, decenyl and other alkenyl groups; aryl groups such as phenyl groups, tolyl groups, and xylyl groups; aralkyl groups such as benzyl groups, phenethyl groups, and 3-phenylpropyl groups; halogenated alkyl groups such as 3-chloropropyl groups and 3,3,3-trifluoropropyl groups; and monovalent hydrocarbon groups such as acryloxy groups, methacryloxy groups, and epoxy groups. From and industrial point of view, the use of hydrolyzable silanes where R is a methyl or phenyl group is suitable.

In the formula, "OA" is a hydrolyzable hydroxyl group, an alkoxy group, or a phenoxy group, and A is independently a hydrogen atom, an alkyl group having 1 to 6 carbon atoms, or a phenyl group. From the viewpoint of condensation reactivity providing the silicone resin, OA is preferably an alkoxy group with 1 to 4 carbon atoms including a hydroxyl group, a methoxy group, an ethoxy group, a propoxy group, and a butoxy group, and in the hydrolyzable silane described above, where OA is in particular preferably an alkoxy group with 1 to 4 carbon atoms.

The silicone resin in the present invention is preferably a silicone resin made up of only a condensation reaction product of two hydrolyzable silanes selected from diorganodialkoxysilane, organotrialkoxysilane, and tetraalkoxysilane, and it is particularly preferred to be a DQ silicone resin made up of only a condensation reaction product of diorganodialkoxysilane and tetraalkoxysilane with a weight ratio within the range of 8:2 to 3:7, and more suitably within the range of 7:3 to 5:5. Particularly suitable examples are DQ silicone resins, which are a condensation reaction product of dimethyldimethoxysilane and tetraethoxysilane.

The coating of the surface of the silicone elastomer particles that uses a condensation reaction product of a hydrolyzable silane is not particularly limited, but may be obtained by hydrolyzing and condensing the hydrolyzable silane described above in the presence of the silicone elastomer particles described above and an alkaline substance in water to coat the surface of the silicone elastomer particles with silicone resin. The timing of the addition of the alkaline substance or acidic substance is arbitrary, but from the viewpoint of uniformly covering the surface of the silicone elastomer particles, an emulsion is preferably formed through emulsification of the crosslink reactive silicone material and hydrolyzable silane that form the silicone elastomer particles described above in water, and the alkaline substance is preferably added to the emulsion after or together with the hydrosilylation reaction of the crosslink reactive silicone.

Suitably, the hydrolyzable silane described above is preferably added to the crosslink reactive silicone material that forms the silicone elastomer particles described above and emulsified in water with uniform mixing using an ordinary agitator such as a propeller blade or flat blade.

From the viewpoint of uniformly coating the surface of the silicone elastomer particles in the emulsion state described above, the temperature of the aqueous reaction solution containing the silicone elastomer particles and the alkaline substance is preferably in the range of 10 to 60° C., and more preferably in the range of 10 to 40° C. Within the above temperature range, the hydrolysis and condensation reactions of the hydrolyzable silane proceeds gently on the surface of the silicone elastomer particles, resulting in a uniform coating with silicone resin. Stirring of the reaction solution is continued until the coating reaction with the desired silicone resin is complete, and may be performed at a temperature higher than the temperature described above (for example, with heating at 40° C. or higher) to complete the reaction.

Alkaline substances or acidic substances act as catalysts for hydrolysis and condensation reactions of hydrolyzable silanes. In the present invention, alkaline substances are preferred, and one type alone or two or more types may be used in combination. The alkaline substance may be added as-is or as an alkaline aqueous solution. The amount of the alkaline substance added is, for an aqueous reaction solution containing silicone elastomer particles and an alkaline substance, an amount that causes the pH of the aqueous dispersion solution containing the alkaline substance to be in the range of 10.0 to 13.0, preferably 10.5 to 12.5. If the pH is outside of said range, the coating of the silicone elastomer particles by the silicone resin made up of the D, T, and Q siloxane units derived from each hydrolyzable silane may be insufficient.

Alkaline substances are not particularly limited, and examples include, alkali metal hydroxides such as potassium hydroxide, sodium hydroxide, and lithium hydroxide; alkaline earth metal hydroxides such as calcium hydroxide and barium hydroxide; alkali metal carbonates such as potassium carbonate and sodium carbonate; ammonia; tetraalkylammonium hydroxides such as tetramethylammonium hydroxide and tetraethylammonium hydroxide; or amines such as monomethylamine, monoethylamine, monopropylamine, monobutylamine, monopentylamine, dimethylamine, diethylamine, trimethylamine, triethanolamine, ethylenediamine; and the like. Among these, ammonia is the most suitable because it can be easily removed from the resulting silicone particulate powder by volatilization. Commercially available aqueous ammonia solutions can be used as ammonia.

After the hydrolysis and condensation reaction described above, the silicone resin coated silicone elastomer particles of the present invention obtained may be used as-is as an aqueous dispersion (aqueous suspension), but suitably, the silicone resin coated silicone elastomer particles are isolated from the reaction solution by removing water. The method of removing water from said aqueous dispersion includes, for example, drying using a vacuum dryer, a hot air circulation oven, or a spray dryer. As a pretreatment for this operation, the dispersion may be concentrated by means of heating and dehydration, filtration separation, centrifugation, decantation, or the like, and if necessary, the dispersion may be washed with water.

In the silicone resin coated silicone elastomer particles of the present invention, the amount of coating with the silicone resin is not particularly limited, but it is particularly preferable that the amount of coating with the silicone resin made up of two types selected from different siloxane units, D, T, and Q, is in the range of 5.0 to 40.0 mass parts for 100 mass parts of the silicone elastomer particles and the range of 5.0 to 20.0 mass parts is particularly preferable. If the amount is less than the lower limit, the amount of coating by the silicone resin may be insufficient, and the technical effects such as uniform dispersibility for organic resins may be insufficient. On the other hand, if the coating amount exceeds the upper limit, the hard physical properties derived from the Q siloxane unit represented by $SiO_{4/2}$ and the T siloxane unit represented by $RSiO_{3/2}$ in the silicone resin are strongly reflected, and the elasticity and elasticity properties derived from the silicone elastomer particles are impaired and when blended into a cosmetic composition, the feel and texture may deteriorate, and when blended into an organic resin, the stress relief properties may decrease.

The amount of coverage by the silicone resin described above can be easily controlled by controlling the amount of the hydrolyzable silane forming the silicone resin added to the crosslinkable composition for forming the silicone elastomer particles described above.

[Silicone Resin Coating of Silicone Elastomer Particles]

In particular, by adopting the suitable manufacturing process described in the next section for the silicone resin coated silicone elastomer particles, the surface of the silicone elastomer particles is uniformly and smoothly coated with a silicone resin consisting of two types selected from differing siloxane units, D, T, and Q, enabling achieving a coating condition of the silicone resin surface with very few protrusions or unevenness. In particular, when spherical silicone elastomer particles are uniformly coated with silicone resin, the smooth surface of the particles suppresses secondary aggregation between the particles and the increase in secondary particle diameter, while at the same time reducing the generation of surface friction, thus achieving stress relief properties and lubricity, as well as a favorable tactile sensation when blended into cosmetics.

[Formation of Silicone Resin Coated Silicone Elastomer Particles]

As a method of forming the silicone resin coated silicone elastomer particles of the present invention using the crosslinkable composition for forming silicone elastomer particles described above, it is suitable to use (a) an organopolysiloxane having at least two alkenyl groups with 2 to 20 carbon atoms in the molecule;

(b) an organohydrogenpolysiloxane having at least two silicon-bonded hydrogen atoms in the molecule; (d) emulsifying the mixture containing the hydrolyzable silane in water; and (c) curing in the presence of a hydrosilylation reaction catalyst to obtain spherical silicone elastomer particles, and simultaneously or after forming the spherical silicone elastomer particles, the surface of the silicone elastomer particles is coated with (d) a silicone resin which is a condensation reaction product of a hydrolyzable silane.

Specifically, the silicone resin coated silicone elastomer particles of the present invention are suitably obtained by a manufacturing method including the following Steps (I), (II) and (III).

Step (I):
A step of emulsifying a mixture containing
(a) an organopolysiloxane having at least two alkenyl groups with 2 to 20 carbon atoms in the molecule,
(b) an organohydrogenpolysiloxane having at least two silicon-bonded hydrogen atoms in the molecule, and
(d) a hydrolyzable silane
in water.

Step (II):
A step of curing the emulsion obtained in Step (I) in the presence of (c) a hydrosilylation reaction catalyst to obtain spherical silicone elastomer particles.

Step (III):
A Step for coating the surface of the silicone elastomer particles with (c) a silicone resin that is a condensation product of a hydrolyzable silane simultaneously with or after Step (II).

The hydrolyzable silanes that are components (a), (b), (c), and component (d) above are the same as those described above.

In the method described above, a mixture containing the crosslinkable composition described above for forming silicone elastomer particles and a hydrolyzable silane is emulsified in an aqueous surfactant solution, and after curing, or together with curing, the surface of the silicone elastomer particles is coated with a silicone resin, and the silicone resin coated silicone elastomer particles can be obtained. In addition, the particle diameter can be easily adjusted by adjusting the emulsion particle diameter. Examples of these surfactants include nonionic, anionic, cationic, and betaine types. The particle diameter of the resulting silicone elastomer particles varies depending on the type and content of the surfactant. In order to prepare silicone elastomer particles having a small particle diameter, the amount of this surfactant added should be in the range of 0.5 to 50 mass parts per 100 mass parts of the crosslinkable composition. On the other hand, in order to prepare silicone elastomer particles having a large particle diameter, the amount of this surfactant added should be in the range of 0.1 to 10 mass parts for 100 mass parts of the crosslinkable composition. The amount of water added as a dispersant should be within the range of 20 to 1,500 mass parts or 50 to 1,000 mass parts for 100 mass parts of the crosslinkable composition.

An emulsifier is preferably used to uniformly disperse the crosslinkable composition for forming silicone elastomer particles described above and hydrolyzable silane in water. Examples of the emulsifying machine include a homomixer, a paddle mixer, a Henschel mixer, a homo-disper, a colloid mill, a propeller agitator, a homogenizer, an in-line continuous emulsifier, an ultrasonic emulsifier, and a vacuum kneading machine.

Next, the aqueous dispersion of the crosslinkable composition for forming silicone elastomer particles containing the hydrolyzable silane, prepared by the method described above, is heated or left at room temperature to cure the crosslinkable silicone elastomer composition in the aqueous dispersion, enabling preparation of the aqueous dispersion of silicone elastomer particles. When the aqueous dispersion of silicone elastomer particles is heated, the heating temperature should be 100° C. or less, and in particular, the heating temperature should be 10 to 95° C. The method of heating the aqueous dispersion of the crosslinkable silicone elastomer composition includes, for example, directly heating the aqueous dispersion and adding the aqueous dispersion to hot water.

Further, with the formation of the aqueous dispersion of the silicone elastomer particles described above, or after formation of the aqueous dispersion of the silicone elastomer particles, the surface of the silicone elastomer particles can be coated with a silicone resin based on a hydrolytic condensation reaction of the hydrolyzable silane contained in the aqueous dispersion. The conditions for coating with silicone resin are as described above.

By coating with the silicone resin described above, an aqueous dispersion of silicone resin coated silicone elastomer particles can be obtained. The aqueous dispersion is stable at room temperature and can be used as-is as a raw material for cosmetics and as an additive for aqueous paints and coatings.

Further, the silicone resin coated silicone elastomer particles can be prepared by removing water from an aqueous dispersion of the silicone resin coated silicone elastomer particles. The method of removing water from said aqueous dispersion includes, for example, drying using a vacuum dryer, a hot air circulation oven, or a spray dryer. The heating and drying temperature of the spray dryer should be set appropriately based on the heat resistance and crosslinking temperature of the silicone resin coated silicone elastomer particles. In order to prevent secondary aggregation of the obtained microparticles, it is preferable to control the temperature of the silicone resin coated silicone elastomer particles below the glass transition temperature of the silicone resin coating the surface thereof. The silicone elastomer particles thus obtained can be recovered by a cyclone, a bag filter or the like.

[Crushing/Classifying Operation]
The silicone resin coated silicone elastomer particles of the present invention are obtained by the method described above. If the silicone resin coated silicone elastomer particles obtained by removal of water or the like are agglomerated, they may preferably be crushed using mechanical force in a pulverizer such as a jet mill, ball mill, hammer mill, or the like. In addition, classification may be performed using a sieve to achieve a specific particle diameter or smaller. In particular, by using mechanical force to crush silicone resin coated silicone elastomer particles containing agglomerates before use, uniform functional particles that do not contain coarse particles can be obtained, and their dispersibility in various organic resins, stress relief properties, and usability when blended in cosmetics can be improved.

[Average Primary Particle Diameter]
The silicone resin coated silicone elastomer particles of the present invention are not particularly limited in terms of their average primary particle diameter, but in the case of an organic resin additive added for the purpose of stress relief of the organic resin, the average primary particle diameter measured using a laser diffraction scattering method is preferably 0.5 to 20 μm and more preferably 0.5 to 15 μm. The particle diameter of the silicone resin coated silicone elastomer particles is controlled according to the silicone elastomer particles before coating, the amount of coating, and the crushing/classification process described above.

[Advantages in the Manufacture of Silicone Resin Coated Silicone Elastomer Particles]

When the silicone resin coated silicone elastomer particles of the present invention are obtained using the manufacturing method described above, the silicone resin coating on the surface of the silicone elastomer particles becomes uniform and smooth, secondary aggregation of the silicone resin coated silicone elastomer particles is suppressed, and problems with workability, such as an increase in agglomerated particle diameter over time do not readily occur. Furthermore, the manufacturing method involves emulsifying a mixture containing a crosslinkable composition for forming silicone elastomer particles and a hydrolyzable silane to form an aqueous dispersion, and then performing the curing reaction and surface coating with silicone resin in the same container (in other words, one pod). The advantage of this method is that it is quicker and more efficient than the conventional method for manufacturing silicone resin coated silicone elastomer particles, in which the silicone elastomer particles before coating are isolated to form a reaction solution, and hydrolyzable silane is dripped into the reaction solution.

[Organic Resin Additives and Organic Resins, Paints, And Coatings]

The silicone resin coated silicone elastomer particles of the present invention have superior uniform dispersibility in organic resins and, if desired, excellent stress relief properties, and the like. In addition, the particles have very excellent workability in that dispersion while blending and adherence on containers do not readily occur. Furthermore, a member, paint film, or coating film produced by curing an organic resin containing said silicone resin coated silicone elastomer particles has improved flexibility (including the softness of the coating layer), durability, and adhesion to and followability of the base material, and is particularly pliable and has superior thermal shock resistance and therefore is extremely useful as a highly functional organic resin, paint, or coating agent for use in electronic materials.

[Organic Resin]

A curable organic resin composition or a thermoplastic resin is suitably exemplified as an organic resin containing the silicone resin coated silicone elastomer particles of the present invention. Of these, curable resins are suitable for electronic materials such as semiconductor substrates. More specifically, examples of the curable organic resin composition include, phenolic resin, formaldehyde resin, xylene resin, xylene-formaldehyde resin, ketone-formaldehyde resin, furan resin, urea resin, imide resin, melamine resin, alkyd resin, unsaturated polyester resin, aniline resin, sulfone-amide resin, silicone resin, epoxy resin, and copolymer resins of these resins, and two or more of these curable resins can be combined. In particular, the curing resin is preferably at least one type selected from the group consisting of an epoxy resin, a phenolic resin, an imide resin, and a silicone resin. The epoxy resin can be any compound containing glycidyl or alicyclic epoxy groups, and examples include o-cresol novolac epoxy resins, phenol novolac epoxy resins, biphenyl epoxy resins, bisphenol A epoxy resins, bisphenol F epoxy resins, dicyclopentadiene epoxy resins, naphthalene epoxy resins, anthracene epoxy resins, naphthol aralkyl epoxy resins, polyvinylphenol epoxy resins, diphenylmethane epoxy resins, diphenylsulfone epoxy resins, triphenolalkane epoxy resins, cresol-naphthol co-condensation epoxy resins, bisphenylethylene epoxy resins, fluorene epoxy resins, stilbene epoxy resins, spiro-coumarone epoxy resins, norbornene epoxy resins, terpene epoxy resins, phenolcyclohexane epoxy resins, halogenated epoxy resins, imide-group-containing epoxy resins, maleimide-group-containing epoxy resins, allyl group-modified epoxy resins, and silicone-modified epoxy resins. Examples of this phenolic resin include a polyvinylphenol type, a phenol novolac type, a naphthol type, a terpene type, a phenol dicyclopentadiene type, a phenol aralkyl type, a naphthol aralkyl type, a triphenol alkane type, a dicyclopentadiene type, a cresol naphthol co-condensation type, and a xylene-naphthol co-condensation type. An example of a silicone resin is an epoxy-modified silicone resin generated by a reaction between an epoxy resin and a silanol group or a silicon-bonded alkoxy group in the silicone resin. Examples of the curing mechanisms of such curable resins are thermal curing, high energy ray curing such as ultraviolet light or radiation, moisture curing, condensation reaction curing, and addition reaction curing. The properties of such curable resins at 25° C. are not limited, and may be in either a liquid state or a solid state that softens upon heating.

The organic resin containing the silicone resin coated silicone elastomer particles of the present invention can be blended with other optional components such as curing agents, curing accelerators, fillers, photosensitizers, higher fatty acid metal salts, ester waxes, plasticizers, and the like. Examples of curing agents include organic acids such as carboxylic acids and sulfonic acids and their anhydrides; organic hydroxy compounds; organosilicon compounds having silanol, alkoxy, or halogeno groups; and primary or secondary amino compounds, and two or more types can be combined. Examples of the curing accelerators include tertiary amine compounds, organometallic compounds such as aluminum and zirconium; organophosphorus compounds such as phosphine; other heterocyclic amine compounds, boron complex compounds, organic ammonium salts, organic sulfonium salts, organic peroxides, and catalysts for hydrosilylation. Examples of these fillers include fibrous fillers such as glass fiber, asbestos, alumina fiber, ceramic fiber composed of alumina and silica, boron fiber, zirconia fiber, silicon carbide fiber, metal fiber, polyester fiber, aramid fiber, nylon fiber, phenolic fiber, natural animal and vegetable fiber; powdered fillers such as fused silica, precipitated silica, fumed silica, calcined silica, zinc oxide, calcined clay, carbon black, glass beads, alumina, talc, calcium carbonate, clay, aluminum hydroxide, barium sulfate, titanium dioxide, aluminum nitride, silicon carbide, magnesium oxide, beryllium oxide, Kaolin, mica, zirconia, and two or more of these can be combined. In the case of epoxy resins, it is particularly preferable to include an amine curing agent.

The silicone resin coated silicone elastomer particles of the present invention may be blended as additives to thermoplastic resins other than those described above, and may be used as modifiers of physical properties such as surface lubricants and stress relief agents, or modifiers of optical properties such as light scattering agents. The type of thermoplastic resin is not particularly limited, and may be at least one polymer selected from a group including a polycarbonate resin, a polyester resin, a polyether resin, a polylactic acid resin, a polyolefin resin such as polyethylene, polypropylene, or an ethylene-propylene copolymer; a polystyrene resin, a styrene copolymer, a fluoropolymer such as tetrafluoroethylene; and a polyvinyl ether, cellulose-based polymers, or a composite resin made up of a combination of these. The silicone resin coated silicone elastomer particles of the present invention can be uniformly dispersed in these thermoplastic resins (including master batches) using a mixing device such as a biaxial or single-axis extruder or a kneader mixer, and may be molded into a desired shape, such as a film form, for use.

The addition amount of the silicone resin coated silicone elastomer particles of the present invention can be selected as appropriate according to the physical properties required of the organic resin, but is generally in the range of 0.1 to 30 mass parts per 100 mass parts of the organic resin, and may be in the range of 0.5 to 10 mass parts. The reason is that if the amount of said particles added is less than said lower limit, the performance such as stress relief properties for the resin or the like may become insufficient, and the pliability and thermal shock resistance of the resulting cured organic resin product may decrease, and in particular, the thermal shock resistance tends to decrease after moisture absorption. On the other hand, if the amount exceeds said upper limit, the organic resin or the paint/coating agent after blending may become thickened and the workability may decrease, and the mechanical properties of the resulting cured organic resin product tend to decrease.

Furthermore, since the silicone resin coated silicone elastomer particles of the present invention are superior in stress relief when blended with an organic resin, they may be blended with an epoxy resin or the like for printed wiring boards to form a prepreg. Furthermore, a copper foil containing filler particles for a printed wiring board equipped with a resin layer containing the silicone resin coated silicone elastomer particles of the present invention on one side of the copper foil can be formed and used for a copper clad laminate (CCL) application.

[Paints, Coating Agents]
Paints and coatings containing the silicone resin coated silicone elastomer particles of the present invention are exemplified as room temperature curing, room temperature drying, and heat curing types, and according to their properties, water-based, oil-based, and powdered types, and according to the vehicle resin, of which polyurethane resin paint, butyral resin paint, long oil phthalate resin paint, alkyd resin paint, amino alkyd resin paint made up of amino resin and alkyd resin, epoxy resin paint, acrylic resin paint, phenol resin paint, silicone modified epoxy resin paint, silicone modified polyester resin paint, and silicone resin paint are examples.

The addition amount of the silicone resin coated silicone elastomer particles of the present invention can be selected as appropriate according to the physical properties required for the paint/coating agent, but in order to impart uniform and soft matting properties to the resulting paint film, the addition amount is preferably within the range of 0.1 to 150 mass parts for 100 mass parts of solid content of the paint, more preferably within the range of 0.1 to 100 mass parts, even more preferably within the range of 0.1 to 50 mass parts, and in particular preferably within the range of 0.1 to 20 mass parts. If the amount of said particles added is less than the lower limit, performance such as matting, adhesion, and stress relief properties of the coating film may be insufficient. If the amount of said particles exceeds the upper limit, the organic resin and the paint/coating agent after blending may become thickened and the workability may decrease.

The paints and coatings containing the silicone resin coated silicone elastomer particles of the present invention may contain alcohols such as methanol and ethanol; ketones such as methyl ethyl ketone and methyl isobutyl ketone; esters such as ethyl acetate, butyl acetate, and cellosolve acetate; amides such as N,N-dimethylformamide; olefins such as hexane, heptane and octane; organic solvents such as aromatic hydrocarbons such as toluene and xylene; known inorganic fillers such as reinforcing silica; organic fillers, curing accelerators, silane coupling agents, pigments such as carbon black; dyes, antioxidants, thickening agents made up of polymer compounds; flame retardants; and weathering agents.

[Cosmetic Composition]
The silicone resin coated silicone elastomer particles of the present invention are also useful as cosmetic raw materials, because part or all of their surface is coated with a silicone resin consisting of two types selected from different siloxane units, D, T, and Q. Compared to conventional silicone elastomer particles and silicone composite particles, these particles have superior oil absorption characteristics and uniform dispersion in other cosmetic components (especially oil-based raw materials). When applied to the skin or hair, these particles suppress oiliness and stickiness of cosmetic materials, spread smoothly, provide a soft tactile sensation, and have a superior sensation during use. In addition, the silicone resin coated silicone elastomer particles of the present invention do not readily scatter and do not readily adhere to containers, making them excellent in workability and compounding stability.

The cosmetic compositions containing the silicone resin coated silicone elastomer particles of the present invention are not particularly limited in type, but include cleaning cosmetics such as soaps, body shampoos, and facial cleansing creams; basic cosmetics such as toners, creams and milks, and packs; base and makeup cosmetics such as powders and foundation; eyebrow cosmetics such as lipstick, cheek rouge, eye shadow, eyeliners, and mascara; makeup cosmetics such as nail polish; hair cosmetics such as shampoos, hair rinses, hairdressing material, hair growth promoters, and hair dye; aromatic cosmetics such as perfume and eau de cologne; toothpaste; bath use products; and special cosmetics such as hair removal agents, shaving lotions, antiperspirants and deodorants, and sunscreen agents. Examples of the dosage forms of these cosmetic compositions include aqueous liquid, oily liquid, emulsion, cream, foam, semi-solid, solid, and powder. These cosmetic compositions can also be used by spraying.

In these cosmetic compositions, the content of the silicone resin coated silicone elastomer particles described above is preferably within the range of 0.5 to 99.0 mass % in the cosmetic composition, and in particular preferably within the range of 1.0 to 95.0 mass %. This is because if the content of the silicone resin coated silicone elastomer particles described above exceeds the upper limit of the range described above, the effect as a cosmetic material will be lost, and if the content is below the lower limit of the range described above, the sensation during use, and the like of the cosmetic composition will not readily be improved.

The silicone resin coated silicone elastomer particles of the present invention can be used in place of all or part of the silicon particles (silicone rubber powder, and the like) proposed in the aforementioned Patent Document 2 (Japanese Unexamined Patent Application No. 2011-105663), Patent Document 3 (Japanese Unexamined Patent Application No. 2011-168634), Patent Document 4 (Japanese Unexamined Patent Application No. 2011-10 2354), Patent Document 5 (International Patent Publication WO2017/191798), and Japanese Unexamined Patent Application No. 2014-122316 or the silicone particles for cosmetic compositions (in particular formulation examples) containing silicone composite particles and there are cases where the sensation during use as well as manufacture efficiency of the cosmetic compositions proposed in these Patent Documents can be further improved.

Furthermore, the silicone resin coated silicone elastomer particles of the present invention can be applied to replace some or all of these silicone particles with respect to the applications and formulations of cosmetic compositions disclosed in the above patents and the like, and use therein is encompassed within the scope of the present application. In addition, the silicone resin coated silicone elastomer particles of the present invention can be used in cosmetic media (aqueous media or oil based media), oil based media (including oils and volatile oils), water, coloring agents, alcohols, water-soluble polymers, film-forming agents, oils, oil-soluble gel agents, organically modified clay minerals, surfactants, resins, salts, moisturizers, preservatives, anti-bacterial agents, antioxidants, pH adjusters, chelating agents, coolants, anti-inflammatory agents, skin brightening agents (such as whitening agents, cell activators, skin roughening agents, blood circulation stimulants, skin astringents, and anti-seborrheic agents), vitamins, amino acids, nucleic acids, hormones, inclusion compounds bioactive substances, medicament active components, fragrances, and the like, disclosed as cosmetic compositions indicated in the Patent Documents described above and may be used in various combinations and is preferred.

In particular, since the silicone resin coated silicone elastomer particles of the present invention have superior oil absorption properties compared to conventionally known silicone particles or silicone composite particles coated with silsesquioxane, and in particular, in cosmetic compositions and formulations containing oil-based cosmetic raw materials such as oils, it achieves favorable sensation during use.

The cosmetic materials of the present invention can be easily manufactured by simply uniformly mixing the cosmetic materials of the present invention and other cosmetic raw materials as described above. As the mixing means, various mixing and kneading devices normally used in the manufacture of cosmetics can be used. Examples of such devices include a homomixer, a paddle mixer, a Henschel mixer, a homodisper, a colloidal mixer, a propeller agitator, a homogenizer, an in-line continuous emulsifier, an ultrasonic emulsifier, and a vacuum kneading machine.

EXAMPLES

The silicone resin coated silicone elastomer particles of the present invention and the manufacturing method thereof will be described in detail by means of examples and comparative examples. However, the present invention is not limited only to these examples. Viscosity in the examples is the value at 25° C. The properties of each silicone particle were measured as follows. In the examples and the like, unless otherwise specified, silicone particles is a generic term for particles made of cured silicone (cured silicone particles), and does not include emulsions.

[JIS A Hardness of Silicone Particles]
The raw material for the silicone elastomer particles, a curable silicone composition, was heated in a heating oven at 150° C. for 1 hour to cure it into a sheet form. The hardness was measured using a JIS A hardness tester as specified in JIS K 6253.

[Average Primary Particle Diameter of Emulsion Particles]
The emulsion before the addition of the platinum catalyst was measured using a laser diffraction particle diameter distribution analyzer (LS-230 from Beckman Coulter), and the median diameter (particle diameter corresponding to 50% of the cumulative distribution, 50% particle diameter) was used as the average particle diameter.

[Average Secondary Particle Diameter of Silicone Particles (Powder)]
Using ethanol as the dispersing medium, the particle diameter of the cured silicone particles was measured with a laser diffraction particle diameter distribution analyzer (Horiba LA-750), and the median diameter of the cured silicone particles in ethanol (particle diameter corresponding to 50% of the cumulative distribution, D90, μm) and the arithmetic dispersion (particle diameter distribution SD, μm2) values were obtained. For the measurement sample, cured silicone particles (1 g) and ethanol (100 mL) were dispersed in a 300 mL cup using stirring blades and an ultrasonic vibrator.

[Uniform Dispersion in Epoxy Resin Solution]
7 g of silicone particles were added to 35 g of an epoxy resin solution (solid content 59.2%), stirred with a homo-disper, and the viscosity of the mixture was measured with a Brookfield E-type viscometer.

The epoxy resin solution was prepared by the following formula.
Flame-retardant epoxy resin (manufactured by DIC, product name "EPICLON 1121N-80M") 434.8 g
Other functional epoxy resin (product name "jER154" manufactured by Mitsubishi Chemical Corporation) 122.3 g
2-Butanone 89.4 g
2-Methoxyethanol 158.6 g The average formulas of component (A) and component (B) used in the examples and comparative examples are listed below.

In the following formula, Vi denotes a vinyl group represented by $CH_2=CH-$, Me denotes a methyl group represented by $CH_3-$, and Hex denotes a hexenyl group represented by $CH_2=C_5\text{-}C_4H_8-$.

$Me_2HexSiO\text{-}(Me_2SiO)_{57}\text{-}(MeHexSiO)_3\text{-}SiHexMe_2$ [Formula 1-1]

The alkenyl group content is 2.7 wt %. Viscosity is 100 mPa·s.

$(Me_2ViSiO)_4Si$ [Formula 1-2]

The alkenyl group content is 23.25 wt %. Viscosity is 3 mPa·s.

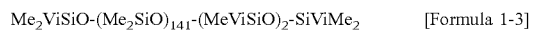

$Me_2ViSiO\text{-}(Me_2SiO)_{141}\text{-}(MeViSiO)_2\text{-}SiViMe_2$ [Formula 1-3]

The alkenyl group content is 1.08 wt %. Viscosity is 370 mPa·s.

$(Me_3SiO_{1/2})_2(Me_2SiO_{2/2})_7(HMeSiO_{2/2})_{11}(MeSiO_{3/2})_1$ [Formula 2-1]

The silicon-bonded hydrogen atom content is 0.825 wt %. Viscosity is 15 mPa·s.

$Me_3SiO_{1/2}\text{-}(Me_2SiO_{2/2})_{39}\text{---}(HMeSiO_{2/2})_{12}\text{---}SiMe_3$ [Formula 2-2]

The silicon-bonded hydrogen atom content is 0.309 wt %. Viscosity is 47 mPa·s.

Example 1

The polyorganosiloxane indicated by the average formula in [Formula 1-1] and the polyorganosiloxane indicated by the average formula in [Formula 2-1] were uniformly mixed at room temperature in a mass ratio of 89:11. 14 mass parts of tetraethoxysilane and 10 mass parts of dimethyldimethoxysilane were added and further mixed. Next, the composition was dispersed in an aqueous solution at 25° C. made up of 3.0 mass parts of polyoxyethylene sorbitan laurate and 20 mass parts of pure water, and further emulsified uniformly using a colloid mill. The average primary particle diameter was 1.4 µm. Then, 350 mass parts of pure water was added for dilution to prepare the emulsion. Next, an isopropyl alcohol solution of platinum chloride (an amount of which platinum metal is set to 10 ppm by mass in this composition) was added to the emulsion as an aqueous dispersion with polyoxyethylene sorbitan laurate and pure water, and stirred, and then the emulsion was let stand at 50° C. for 1 hour to perform the hydrosilylation reaction. Subsequently, 20 mass parts of 28% ammonia water were added. The pH of the solution at this time was 11. The silane was let stand for another hour to allow the condensation reaction of the silane to occur, and a uniform aqueous suspension of silicone rubber particles coated with silicone resin was prepared. Next, the aqueous suspension was dried using a small spray dryer (manufactured by Ashizawa Niro) to obtain silicone resin coated silicone elastomer particles. The JIS-A hardness of the obtained silicone elastomer particles was 68, and their average secondary particle diameter was 2.2 µm.

Example 2

The polyorganosiloxane indicated by the average formula in [Formula 1-2] and the polyorganosiloxane indicated by the average formula in [Formula 2-2] were uniformly mixed at room temperature in a mass ratio of 25:75. 9 mass parts of tetraethoxysilane and 4 mass parts of dimethyldimethoxysilane were added and further mixed. Next, the composition was dispersed in an aqueous solution at 25° C. made up of 3.0 mass parts of polyoxyethylene sorbitan laurate and 20 mass parts of pure water, and further emulsified uniformly using a colloid mill. The average primary particle diameter was 1.4 µm. Then, 350 mass parts of pure water was added for dilution to prepare the emulsion. Next, an isopropyl alcohol solution of platinum chloride (an amount of which platinum metal is set to 10 ppm by mass in this composition) was added to the emulsion as an aqueous dispersion with polyoxyethylene sorbitan laurate and pure water, and stirred, and then the emulsion was let stand at 50° C. for 3 hours to perform the hydrosilylation reaction. Subsequently, 20 mass parts of 28% ammonia water was added. The pH of the solution at this time was 11. The silane was let stand for another hour to allow the condensation reaction of the silane to occur, and a uniform aqueous suspension of silicone rubber particles coated with silicone resin was prepared. Next, the aqueous suspension was dried using a small spray dryer (manufactured by Ashizawa Niro) to obtain silicone resin coated silicone elastomer particles. The JIS-A hardness of the obtained silicone elastomer particles was 83, and their average secondary particle diameter was 3.2 µm.

Example 3

The polyorganosiloxane indicated by the average formula in [Formula 1-3] and the polyorganosiloxane indicated by the average formula in [Formula 2-1] were uniformly mixed at room temperature in a mass ratio of 96:4. 14 mass parts of tetraethoxysilane and 10 mass parts of dimethyldimethoxysilane were added and further mixed. Next, the composition was dispersed in an aqueous solution at 25° C. made up of 3.0 mass parts of polyoxyethylene sorbitan laurate and 20 mass parts of pure water, and further emulsified uniformly using a colloid mill. The average primary particle diameter was 1.1 µm. Then, 350 mass parts of pure water was added for dilution to prepare the emulsion. Next, an isopropyl alcohol solution of platinum chloride (an amount of which platinum metal is set to 10 ppm by mass in this composition) was added to the emulsion as an aqueous dispersion with polyoxyethylene sorbitan laurate and pure water, and stirred, and then the emulsion was let stand at 50° C. for 3 hours to perform the hydrosilylation reaction. Subsequently, 20 mass parts of 28% ammonia water was added. The pH of the solution at this time was 11. The silane was let stand for another hour to allow the condensation reaction of the silane to occur, and a uniform aqueous suspension of silicone rubber particles coated with silicone resin was prepared. Next, the aqueous suspension was dried using a small spray dryer (manufactured by Ashizawa Niro) to obtain silicone resin coated silicone elastomer particles. The JIS-A hardness of the obtained silicone elastomer particles was 50, and their average secondary particle diameter was 4.0 µm.

Example 4

The polyorganosiloxane indicated by the average formula in [Formula 1-1] and the polyorganosiloxane indicated by the average formula in [Formula 2-1] were uniformly mixed at room temperature in a mass ratio of 89:11. 14 mass parts of tetraethoxysilane and 7 mass parts of diphenyldimethoxysilane were added and further mixed. Next, this composition was dispersed in an aqueous solution at 25° C. made up of 3 mass parts of polyoxyethylene alkyl (C12-14) ether and 20 mass parts of pure water, and further emulsified uniformly using a colloid mill. The average primary particle diameter was 0.9 µm. Then, 350 mass parts of pure water was added for dilution to prepare the emulsion. Next, an isopropyl alcohol solution of platinum chloride (an amount of which platinum metal set to 10 ppm by mass in this composition) was added to the emulsion as an aqueous dispersion with polyoxyethylene alkyl (C12-14) ether and pure water, and stirred, and then the emulsion was let stand at 50° C. for 1 hour to perform the hydrosilylation reaction. Subsequently, 20 mass parts of 28% ammonia water was added. The pH of the solution at this time was 11. The silane was let stand for another hour to allow the condensation reaction of the silane to occur, and a uniform aqueous suspension of silicone rubber particles coated with silicone resin was prepared. Next, the aqueous suspension was dried using a small spray dryer (manufactured by Ashizawa Niro) to obtain silicone resin coated silicone elastomer particles. The JIS-A hardness of the obtained silicone elastomer particles was 68, and their average secondary particle diameter was 1.6 µm.

Comparative Example 1

The polyorganosiloxane indicated by the average formula in [Formula 1-1] and the polyorganosiloxane indicated by the average formula in [Formula 2-1] were uniformly mixed at room temperature in a mass ratio of 89:11. Next, this composition was dispersed in an aqueous solution at 25° C. made up of 3 mass parts of polyoxyethylene alkyl (C12-14) ether and 20 mass parts of pure water, and further emulsified uniformly using a colloid mill. The average primary particle diameter was 1.5 µm. Then, 350 mass parts of pure water was added for dilution to prepare the emulsion. Next, an isopropyl alcohol solution of platinum chloride (an amount of which platinum metal set to 10 ppm by mass in this composition) was added to the emulsion as an aqueous dispersion with polyoxyethylene alkyl (C12-14) ether and pure water, and the emulsion was stirred. Subsequently, the silicone rubber was let stand at 50° C. for 1 hour to prepare a uniform aqueous suspension of silicone rubber particles. Next, the aqueous suspension was dried using a small spray dryer (manufactured by Ashizawa Niro) to obtain silicone elastomer particles. The JIS-A hardness of the obtained silicone elastomer particles was 68, and their average secondary particle diameter was 3.1 µm.

Comparative Example 2

The polyorganosiloxane indicated by the average formula in [Formula 1-2] and the polyorganosiloxane indicated by the average formula in [Formula 2-2] were uniformly mixed at room temperature in a mass ratio of 25:75. Next, this composition was dispersed in an aqueous solution at 25° C. made up of 3.0 mass parts of polyoxyethylene alkyl (C12-14) ether and 20 mass parts of pure water, and further emulsified uniformly using a colloid mill. The average primary particle diameter was 1.3 µm. Then, 350 mass parts of pure water was added for dilution to prepare the emulsion. Next, an isopropyl alcohol solution of platinum chloride (an amount of which platinum metal set to 10 ppm by mass in this composition) was added to the emulsion as an aqueous dispersion with polyoxyethylene alkyl (C12-14) ether and pure water, and the emulsion was stirred. Subsequently, the silicone rubber was let stand at 50° C. for 3 hours to prepare a uniform aqueous suspension of silicone rubber particles. Next, the aqueous suspension was dried using a small spray dryer (manufactured by Ashizawa Niro) to obtain silicone elastomer particles. The JIS-A hardness of the obtained silicone elastomer particles was 83, and their average secondary particle diameter was 4.6 µm.

Comparative Example 3

The polyorganosiloxane indicated by the average formula in [Formula 1-3] and the polyorganosiloxane indicated by the average formula in [Formula 2-1] were uniformly mixed at room temperature in a mass ratio of 96:4. Next, this composition was dispersed in an aqueous solution at 25° C. made up of 3.0 mass parts of polyoxyethylene alkyl (C12-14) ether and 20 mass parts of pure water, and further emulsified uniformly using a colloid mill. The average primary particle diameter was 1.5 µm. Then, 350 mass parts of pure water was added for dilution to prepare the emulsion. Next, an isopropyl alcohol solution of platinum chloride (an amount of which platinum metal set to 10 ppm by mass in this composition) was added to the emulsion as an aqueous dispersion with polyoxyethylene alkyl (C12-14) ether and pure water, and the emulsion was stirred. Subsequently, the silicone rubber was let stand at 50° C. for 3 hours to prepare a uniform aqueous suspension of silicone rubber particles. Next, the aqueous suspension was dried using a small spray dryer (manufactured by Ashizawa Niro) to obtain silicone elastomer particles. The JIS-A hardness of the obtained silicone elastomer particles was 50, and their average secondary particle diameter was 56.7 µm.

Comparative Example 4

The polyorganosiloxane indicated by the average formula in [Formula 1-1] and the polyorganosiloxane indicated by the average formula in [Formula 2-1] were uniformly mixed at room temperature in a mass ratio of 89:11. Next, this composition was dispersed in an aqueous solution at 25° C. made up of 3.0 mass parts of polyoxyethylene alkyl (C12-14) ether and 20 mass parts of pure water, and further emulsified uniformly using a colloid mill. The average primary particle diameter was 1.0 µm. Then, 350 mass parts of pure water was added for dilution to prepare the emulsion. Next, an isopropyl alcohol solution of platinum chloride (an amount of which platinum metal set to 10 ppm by mass in this composition) was added to the emulsion as an aqueous dispersion with polyoxyethylene alkyl (C12-14) ether and pure water, and the emulsion was stirred. Subsequently, the silicone rubber was let stand at 50° C. for 1 hour to prepare a uniform aqueous suspension of silicone rubber particles. The JIS-A hardness of the obtained silicone elastomer particles was 68, and their average primary particle diameter was 1.0 µm.

500 g of the aqueous dispersion of silicone elastomer particles obtained in Preparation Example 1 was transferred to a 2 L glass flask provided with a stirring device equipped with a stirring blade, and 500 g of water and 20 g of 28% ammonia water were added. The pH of the solution at this time was 11. After adjusting the temperature to 5 to 10° C., 35 g of tetraethoxysilane (the amount of silicone resin made up of siloxane units represented by $SiO_{4/2}$ after hydrolysis and condensation reaction is 15 mass parts for 100 mass parts of silicone elastomer particles before coating) was dripped in over 30 minutes, and the mixture was stirred for an additional hour. During this time, the liquid temperature was maintained at 5 to 10° C. Next, the mixture was heated to 55 to 60° C. and stirred for 1 hour while maintaining the temperature to complete the hydrolysis and condensation reaction of the tetraethoxysilane.

The resulting silicone elastomer particles/tetraethoxysilane hydrolysis and condensation reaction solution was filtered. The dehydrated material was transferred to a stainless steel tray and dried in a hot air circulating dryer at a temperature of 105° C. The dried material was crushed in a jet mill to obtain microparticles with flowability. When the microparticles were observed under an electron microscope, it was confirmed that they were spherical particles, the particle surfaces thereof being coated with silicone resin, and that they were silicone resin coated silicone elastomer particles where the surfaces were coated with silicone resin made up of siloxane units represented by $SiO_{4/2}$. The average primary particle diameter of the obtained silicone resin coated silicone elastomer particles was 5.3 µm.

Example 5

The polyorganosiloxane indicated by the average formula in [Formula 1-1] and the polyorganosiloxane indicated by the average formula in [Formula 2-1] were uniformly mixed at room temperature in a mass ratio of 89:11. 3 weight parts of dimethyl dimethyldimethoxysilane and 16 weight parts of methyltrimethoxysilane were added and further mixed. The composition was then dispersed in an aqueous solution at 25° C. containing 3 mass parts of polyoxyethylene sorbitan laurate and 20 mass parts of pure water, and further emulsified uniformly using a colloid mill. The average primary particle diameter was 1.3 µm. Then, 350 mass parts of pure water was added for dilution to prepare the emulsion. Next, an isopropyl alcohol solution of platinum chloride (an amount of which platinum metal is set to 10 ppm by mass in this composition) was added to the emulsion as an aqueous dispersion with polyoxyethylene sorbitan laurate and pure water, and stirred, and then the emulsion was let stand at 50° C. for 1 hour to perform the hydrosilylation reaction. Subsequently, 20 mass parts of 28% ammonia water were added. The pH of the solution at this time was 11. The silane was let stand for another hour to allow the condensation reaction of the silane to occur, and a uniform aqueous suspension of silicone rubber particles coated with silicone resin was prepared. Next, the aqueous suspension was dried using a small spray dryer (manufactured by Ashizawa Niro) to obtain silicone resin coated silicone elastomer particles. The JIS-A hardness of the obtained silicone elastomer particles was 68, and their average secondary particle diameter was 2.5 µm.

Example 6

The polyorganosiloxane indicated by the average formula in [Formula 1-1] and the polyorganosiloxane indicated by the average formula in [Formula 2-1] were uniformly mixed at room temperature in a mass ratio of 89:11. 16 mass parts of methyltrimethoxysilane and 7 mass parts of tetraethoxysilane were added and further mixed. The composition was then dispersed in an aqueous solution at 25° C. containing 3 mass parts of polyoxyethylene sorbitan laurate and 20 mass parts of pure water, and further emulsified uniformly using a colloid mill. The average primary particle diameter was 1.0 µm. Then, 350 mass parts of pure water was added for dilution to prepare the emulsion. Next, an isopropyl alcohol solution of platinum chloride (an amount of which platinum metal is set to 10 ppm by mass in this composition) was added to the emulsion as an aqueous dispersion with polyoxyethylene sorbitan laurate and pure water, and stirred, and then the emulsion was let stand at 50° C. for 1 hour to perform the hydrosilylation reaction. Subsequently, 20 mass parts of 28% ammonia water were added. The pH of the solution at this time was 11. The silane was let stand for another hour to allow the condensation reaction of the silane to occur, and a uniform aqueous suspension of silicone rubber particles coated with silicone resin was prepared. Next, the aqueous suspension was dried using a small spray dryer (manufactured by Ashizawa Niro) to obtain silicone resin coated silicone elastomer particles. The JIS-A hardness of the obtained silicone elastomer particles was 68, and their average secondary particle diameter was 1.6 µm.

The properties of Examples 1 to 6 and Comparative Examples 1 to 4 are shown in Table 1. The chemical species of the silalkylene bonds between the silicon atoms in the silicone elastomer particles, the JIS hardness in the absence of coating, and the type of silicone resin used to coat the silicone elastomer particle surface (siloxane units represented by D, Q, and T) are shown in the table.

TABLE 1

| | Silalkylene bond | JIS hardness | Coated silicone resin | Average primary particle diameter (µm) | Average secondary particle diameter (µm) | Epoxy Resin Mix Viscosity (mPa)-s |
|---|---|---|---|---|---|---|
| Example 1 | Hexylene (C6) | 68 | D, Q | 1.4 | 2.2 | 280 |
| Example 2 | Ethylene (C2) | 83 | D, Q | 1.4 | 3.2 | 460 |
| Example 3 | Ethylene (C2) | 50 | D, Q | 1.1 | 4.0 | 790 |
| Example 4 | Hexylene (C6) | 68 | D*, Q | 0.9 | 1.6 | 290 |
| Comparative Example 1 | Hexylene (C6) | 68 | — | 1.5 | 3.1 | 830 |
| Comparative Example 2 | Ethylene (C2) | 83 | — | 1.3 | 4.6 | 640 |
| Comparative Example 3 | Ethylene (C2) | 50 | — | 1.5 | 56.7 | Separated |
| Comparative Example 4 | Hexylene (C6) | 68 | Q | 1.4 | 35.8 | 3440 |
| Example 5 | Hexylene (C6) | 68 | D, T | 1.3 | 2.5 | 390 |
| Example 6 | Hexylene (C6) | 68 | T, Q | 1.0 | 1.6 | 270 |

*D siloxane unit containing a diphenyl group

[Summary]

Figure 2:
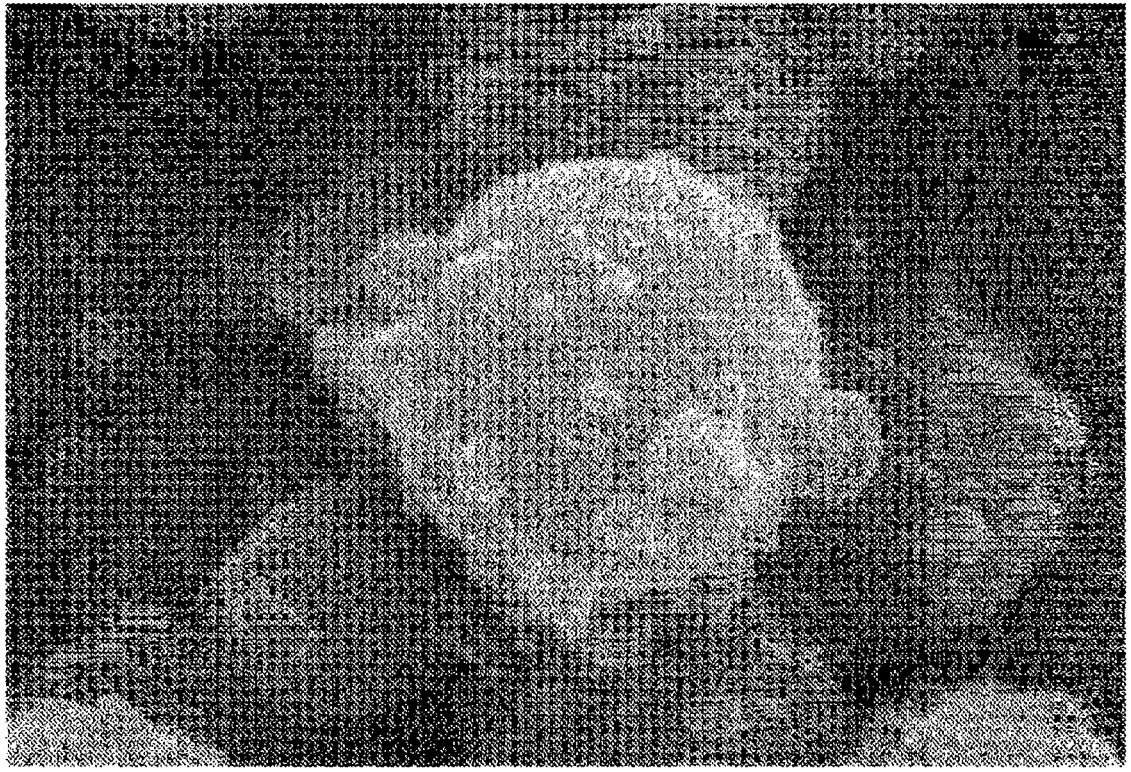
FIG. 2 is an electron photomicrograph of silicone resin coated silicone elastomer particles of Comparative Example 4

When the hexylene cross-linked silicone elastomer particles having the same JIS hardness are compared, in Examples 1, 4, 5, and 6, the average secondary particle diameters are all less than 2.5 µm, and the mixing viscosity with epoxy resin is also kept low, whereas in Comparative Example 1, which is uncoated, and in Comparative Example 4, which is coated only with Q-siloxane units in contrast, the average secondary particle diameter increased, agglomeration readily occurred, and the mixing viscosity with epoxy resin also increased significantly. In particular, when Example 1 and Comparative Example 4 are contrasted using electron photomicrographs (FIG. 1, FIG. 2), the coating state of Example 1 is uniform and smooth, whereas Comparative Example 4 has many protrusions and unevenness, and the particle surface conditions are clearly different.

A similar trend was confirmed when Examples 2 and 3, which are ethylene crosslinked silicone elastomer particles, were contrasted with Comparative Examples 2 and 3. In other words, by selecting the coating with the silicone resin of the present invention, it was possible to achieve silicone resin coated silicone elastomer particles that suppressed the increase in average secondary particle diameter, solved the problem of agglomeration, and had excellent dispersibility in organic resins.

Formulation Examples

The silicone resin coated silicone elastomer particles of the present invention can be used in place of all or part of the silicon particles (silicone rubber powder, and the like) or the silicone particles for cosmetic compositions (in particular formulation examples) containing silicone composite particles proposed in the aforementioned Patent Document 2 (Japanese Unexamined Patent Application No. 2011-105663), Patent Document 3 (Japanese Unexamined Patent Application No. 2011-168634), Patent Document 4 (Japanese Unexamined Patent Application No. 2011-10 2354), Patent Document 5 (International Patent Publication WO2017/191798), and Japanese Unexamined Patent Application No. 2014-122316.

The following are examples of formulations in which the silicone resin coated silicone elastomer particles of the present invention can be used, but the formulations of the cosmetic materials of the present invention are not limited thereto. In the following formulation examples, "the silicone resin coated silicone elastomer particles of the examples" may be a mixture of the silicone resin coated silicone elastomer particles of any of Examples 1 to 6 or a plurality of examples of the present application.

Formulation Example 1: W/O Cream Foundation (Component)
Phase A
Cetyl diglyceryl tris(trimethylsiloxy)silylethyl Dimethicone (Note 1) 5.0 mass parts
2) Dimethicone (Note 2) 4.2 mass parts
3) Ethylhexyl methoxysilicate (Note 3) 3.3 mass parts
4) Caprylyl methicone (Note 4) 3.3 mass parts
5) Isododecane, (dimethicone/bis-isobutyl PPG-20) cross polymer (Note 5) 1.5 mass parts
6) Silicone resin coated silicone elastomer particles of the examples 2.0 mass parts
Phase B
7) Titanium oxide, talc, methicone (Note 6) 4.71 mass parts
8) Mica, aluminum hydroxide (Note 7) 2.46 mass parts
9) Iron oxide yellow (Note 8) 0.66 mass parts
10) Iron oxide red (Note 9) 0.16 mass parts
11) Iron oxide black (Note 10) 0.006 mass parts
12) Cetyl diglyceryl tris (trimethylsiloxy) silylethyl ester Dimethicone (Note 11) 0.5 mass parts
13) Caprylyl methicone (Note 12) 3.7 mass parts
Phase C
14) Purified water 61.5 mass parts
15) BG 8.0 mass parts
16) Sodium chloride 1.0 mass parts
Note 1: ES-5600 Silicone Glycerol Emulsifier manufactured by Dow Corning Toray Co., Ltd.
Note 2: PMX-200 SILICONE FLUID 2CS manufactured by Dow Corning Toray Co., Ltd.
Note 3: Neo Heliopan AV manufactured by Symrise
Note 4: FZ-3196 manufactured by Dow Corning Toray Co., Ltd.
Note 5: EL-8050 ID Silicone Organic Elastomer Blend manufactured by Dow Corning Toray Co., Ltd.
Note 6: SA Titan CR-50 manufactured by Miyoshi Kasei, Inc.
Note 7: SA Exel Mica JP-2 manufactured by Miyoshi Kasei, Inc.
Note 8: SA Yellow UXLO manufactured by Miyoshi Kasei, Inc.
Note 9: SA Red manufactured by Miyoshi Kasei, Inc.
Note 10: SA Black manufactured by Miyoshi Kasei, Inc.
Note 11: ES-5600 Silicone Glycerol Emulsifier manufactured by Dow Corning Toray Co., Ltd.
Note 12: FZ-3196 manufactured by Dow Corning Toray Co., Ltd.

The W/O cream foundation of formulation example 1 is adjusted according to the following procedures.
1. Mix components 1 to 6 until uniform.
2. Mix 3 rolls of components 7 to 13.
3. Mix components 14 to 16.
4. Mix 1 and 2 above.
5. Add 3 above while stirring 4 above vigorously, and emulsify.

Formulation Example 2: O/W Foundation (Component)
Phase A
1) Silicone resin coated silicone elastomer particles of the examples 18 mass parts
2) Talc (Note 1) 18 mass parts
Phase B
3) Purified water 20 mass parts
4) Glycerin 10 mass parts Phase C
5) Sodium polyacrylate, dimethicone (Note 2) 1 mass part
6) DMDM hydantoin, propynyl butylcarbamate iodide (Note 3) q.s.
7) Ethylhexyl salicylate (Note 4) 3 mass parts
8) Ethylhexyl methoxysilicate (Note 5) 3 mass parts
Phase D
9) Purified water 21 mass parts
Phase E
10) Caprylyl methicone (Note 6) 2 mass parts
11) Iron oxide black, dimethicone (Note 7) 0.05 mass parts
12) Iron oxide red, dimethicone (Note 8) 0.1 mass parts
13) Iron oxide yellow, dimethicone (Note 9) 0.25 mass parts
14) Titanium oxide, talc, dimethicone (Note 10) 3.6 mass parts
Note 1: Si talc manufactured by Miyoshi Kasei, Inc.
Note 2: RM 2051 Rheology Modifier manufactured by Dow Corning Toray Co., Ltd.
Note 3: Glydant Plus manufactured by Lonza Group
Note 4: Neo Heliopan OS manufactured by Symrise
Note 5: Escalol 557 manufactured by ISP
Note 6: FZ-3196 manufactured by Dow Corning Toray Co., Ltd.
Note 7: SA-Black BL-100 manufactured by Miyoshi Kasei
Note 8: SA-Bengara Cloisonne by Miyoshi Kasei
Note 9: SI-YELLOW-LLXLO manufactured by Miyoshi Kasei
Note 10: SI-Titanium CR-50 manufactured by Miyoshi Kasei The O/W cream foundation of formulation example 2 is adjusted according to the following procedures.
1. Mix components 1 and 2.
2. Mix components 3 and 4.
3. Mix 1 and 2 above.
4. Mix components 5 to 8.
5. Add component 9 to 4 described above and mix.
6. Mix components 10 to 14 until homogeneous.
7. Mix all components together.

Formulation Example 3: W/O BB Cream (Component)
Phase A
1) Lauryl PEG-10tris(trimethylsiloxy)silylethyldimethicone (Note 1) 3 mass parts
2) Caprylyl methicone (Note 2) 14 mass parts
3) Ethylhexyl methoxysilicate (Note 3) 7.5 mass parts
4) Hexyl diethylaminohydroxybenzoylbenzoate (Note 4) 1.5 mass parts
5) Ethylhexyl salicylate 2.5 mass parts
6) Trimethylsiloxysilicate acid, polypropylene silsesquioxane (Note 5) 2 mass parts
7) Silicone resin coated silicone elastomer particles of the examples 4 mass parts
8) Phenyl trimethicone (Note 6) 4 mass parts
Phase B
9) Glycerin 8 mass parts
10) Sodium chloride 0.7 mass parts
11) Purified water 40.8 mass parts
Phase C
12) Titanium oxide 5.6 mass parts
13) Iron oxide yellow (Note 7) 0.25 mass parts
14) Iron oxide red (Note 8) 0.1 mass parts
15) Iron oxide black (Note 9) 0.05 mass parts
16) Phenyl trimethicone (Note 10) 5.2 mass parts 17) Zinc oxide (Note 11) 0.8 mass parts
18) Lauryl PEG-10 Tris(trimethylsiloxy)silylethyl Dimethicone 1 mass part Note 1: ES-5300 Formulation Aid manufactured by Dow Corning Toray Co., Ltd.
Note 2: FZ-3196 manufactured by Dow Corning Toray Co., Ltd.
Note 3: Uvinyl MC80N manufactured by BASF
Note 4: Ubinal A Plus Glanular manufactured by BASF
Note 5: MQ-1640 Flake Resin manufactured by Dow Corning Toray Co., Ltd.
Note 6: SH556 manufactured by Dow Corning Toray Co., Ltd.
Note 7: SA-IOY-8 manufactured by Miyoshi Kasei, Inc.
Note 8: SA-IOR-8 manufactured by Miyoshi Kasei, Inc.
Note 9: SA-IOB-8 manufactured by Miyoshi Kasei, Inc.
Note 10: SH556 manufactured by Dow Corning Toray Co., Ltd.
Note 11: FINEX-30S-LPT manufactured by Sakai Chemical Industry Co., Ltd.
Note 12: ES-5300 Formulation Aid manufactured by Dow Corning Toray Co., Ltd.

The W/O BB Cream of formulation example 3 is adjusted according to the following procedures.
1. Mix components 1 to 8.
2. Mix components 9 to 11.
3. Mix components 12 to 18.
4. Mix 1 above and 3 above.
5. While vigorously stirring 1 above, slowly add 2 above to emulsify.

Formulation Example 4: Nonaqueous Foundation (Component)
Phase A
1) Titanium oxide, dimethicone (Note 1) 49.23 mass parts
2) Iron oxide yellow, dimethicone (Note 2) 9.86 mass parts
3) Iron oxide red, dimethicone (Note 3) 1.97 mass parts
4) Iron oxide black, dimethicone (Note 4) 0.55 mass parts
5) Cetyl diglyceryl tris(trimethylsiloxy)silylethyl dimethicone (Note 5) 1.58 mass parts
6) Caprylyl methicone (Note 6) 15.8 mass parts
Phase B
7) Silicone resin coated silicone elastomer particles of the examples 2 mass parts
8) Cyclopentasiloxane (Note 7) 13 mass parts
9) Isododecane, (acrylate/polytrimethylsiloxy methacrylate) copolymer (Note 8) 5 mass parts
10) Disteardimonium hectorite (Note 9) 1 mass part Note 1: SI-Titanium CR-50 manufactured by Miyoshi Kasei, Inc.
Note 2: SI-YELLOW-LLXLO manufactured by Miyoshi Kasei, Inc.
Note 3: SA-Bengara Cloisonne manufactured by Miyoshi Kasei, Inc.
Note 4: SA-Black BL-100 manufactured by Miyoshi Kasei, Inc.
Note 5: ES-5600 Silicone Glycerol Emulsifier manufactured by Dow Corning Toray Co., Ltd.
Note 6: FZ-3196 manufactured by Dow Corning Toray Co., Ltd.
Note 7: SH245 manufactured by Dow Corning Toray Co., Ltd.
Note 8: FA 4002 ID Silicone Acrylate manufactured by Dow Corning Toray Co., Ltd.
Note 9: Bentone (R) 38 V CG manufactured by Elementis The non-aqueous foundation of formulation example 4 is adjusted according to the following procedures.
1. Mix components 1 to 6.
2. Mix components 7 to 10.
3. Mix 1 and 2 above.

Formulation Example 5: Compact Foundation (Component)
1) Talc (Note 1) 20 mass parts
2) Mica (Note 2) 34.6 mass parts
3) Titanium oxide (Note 3) 10 mass parts
4) Iron oxide red (Note 4) 1 mass part
5) Iron oxide yellow (Note 5) 4 mass parts
6) Iron oxide black (Note 6) 0.4 mass parts
7) Mica (Note 7) 15 mass parts
8) Polystyrene (Note 8) 5 mass parts
9) Squalane: 3 mass parts
10) Octyldodecyl myristate (Note 9) 1.2 mass parts
11) Vaseline 2.5 mass parts
12) Dimethicone (Note 10) 3.3 mass parts
13) Silicone resin coated silicone elastomer particles of the examples 5 mass parts Note 1: SI Talc manufactured by Miyoshi Kasei, Inc.
Note 2: SI-SERICITE FSE manufactured by Miyoshi Kasei, Inc.
Note 3: SI-Titan CR-50 manufactured by Miyoshi Kasei, Inc.
Note 4: SA Red manufactured by Miyoshi Kasei, Inc.
Note 5: SA Yellow UXLO manufactured by Miyoshi Kasei, Inc.
Note 6: SA Black manufactured by Miyoshi Kasei, Inc.
Note 7: SA-Excel Mica JP-2 manufactured by Miyoshi Kasei, Inc.
Note 8: Fine pearl 3000SPQ manufactured by Sumitomo Chemical Co., Ltd.
Note 9: EXCEPARL OD-M manufactured by Kao Corporation
Note 10: SH200-5000cs manufactured by Dow Corning Toray Co., Ltd.

The compact foundation of formulation example 5 is adjusted according to the following procedures.
1. Mix all of the above.

Formulation Example 6: W/O Skin Cream (Component)
Phase A
1) Lauryl PEG/PPG-18/18 dimethicone (Note 1) 2 mass parts
2) Bis(hydroxyethoxypropyl)dimethicone (Note 2) 2 mass parts
3) Isopropyl palmitate (Note 3) 1 mass part
4) Cyclopentasiloxane (Note 4) 6.5 mass parts
5) Mineral oil (Note 5) 10 mass parts
6) Vaseline 1.5 mass parts
7) Silicone resin coated silicone elastomer particles of the examples 5 mass parts
Phase B
8) Glycerin 5 mass parts
9) Sodium chloride 1 mass part
10) Purified water 66 mass parts Note 1: 5200 Formulation Aid manufactured by Dow Corning Toray Co., Ltd.
Note 2: 5562 Carbinol Fluid manufactured by Dow Corning Toray Co., Ltd.
Note 3: Excipal IPM manufactured by Kao Corporation Note 4: SH245 manufactured by Dow Corning Toray Co., Ltd.

Note 5: Hycor K-230 manufactured by Kaneda Co., Ltd.

The W/O skin cream of formulation example 6 is adjusted according to the following procedures.
1. Mix components 1 to 7.
2. Mix components 8 to 10.
3. While vigorously stirring 1 above, slowly add 2 above to emulsify.

Formulation Example 7: Sunscreen Non-Aqueous Lotion (Component)
1) Zinc oxide (Note 1) 6 mass parts
2) Lauryl PEG-10 tris(trimethylsiloxy)silylethyl dimethicone (Note 2) 0.5 mass parts
3) Hexadecane 3.5 mass parts
4) Ethylhexyl methoxysilicate (Note 3) 7.5 mass parts
5) Dimethicone, dimethicone cross polymer (Note 4) 24 mass parts
6) Cyclopentasiloxane (Note 5) 60.5 mass parts
7) Silicone resin coated silicone elastomer particles of the examples 2 mass parts Note 1: FINEX-30S-LPT manufactured by Sakai Chemical Industry Co., Ltd.
Note 2: ES-5300 Formulation Aid manufactured by Dow Corning Toray Co., Ltd.
Note 3: Uvinyl MC80N manufactured by BASF
Note 4: 9041 Silicone Elastomer Blend manufactured by Dow Corning Toray Co., Ltd.
Note 5: SH245 manufactured by Dow Corning Toray Co., Ltd.

The sunscreen non-aqueous lotion of formulation example 7 is prepared by the following procedures.
1. Mix components 1 to 3 (bead mill and the like).
2. Add components 4 to 7 to the above components and stir until uniform.

Formulation Example 8: O/W Wrinkle Care Cream (Component)
Phase A
1) Cyclopentasiloxane (Note 1) 11 mass parts
2) Silicone resin coated silicone elastomer particles of the examples 10 mass parts
3) Lauryl PEG/PPG-18/18 dimethicone (Note 2) 0.5 mass parts
4) PEG-12 dimethicone (Note 3) 4 mass parts
Phase B
5) Purified water 72.5 mass parts
Phase C
6) Polyacrylamide, water, (C13,14) isoparaffin, laureth-7 (Note 4) 2 mass parts Note 1: SH245 manufactured by Dow Corning Toray Co., Ltd.
Note 2: 5200 Formulation Aid manufactured by Dow Corning Toray Co., Ltd.
Note 3: OFX-5329 manufactured by Dow Corning Toray Co., Ltd.
Note 4: SEPPIC S.A. Simulgel 305 manufactured by Simulgel Inc.

The O/W Wrinkle Care Cream of formulation example 8 is adjusted according to the following procedures.
1. Mix components 1 to 4 until uniform.
2. Mix components 4 and 5 until uniform.
3. Add 1 to 2 above and mix until uniform.

Formulation Example 9: Toner (Component)
Phase A
1. Silicone emulsifier premix *1 7.0 weight parts
2. Trilaureth-4-phosphoric acid*2 0.05 weight parts
3. Ethanol 2.0 weight parts
Phase B
4. Water: remainder
5. Butylene glycol (BG) 3.0 weight parts
6. Glycerin 6.0 weight parts
7. Dipropylene glycol (DPG) 2.0 weight parts
8. Disodium hydrogen phosphate 0.01 weight parts
9. Sodium dihydrogen phosphate 0.01 weight parts
10. Preservatives q.s.
11. Silicone resin coated silicone elastomer particles of the examples 5.0 weight parts

*1 FB-2540 Emulsifier Blend manufactured by Dow Corning Toray Co., Ltd.
*2 Hostafat KL340D manufactured by Clariant (Method of Preparation)
1. MIX PHASE A.
2. MIX PHASE B.
3. SLOWLY ADD PHASE A WHILE STIRRING PHASE B.

Formulation Example 10: W/O Sunscreen (Component)
Phase A
1. Silicone emulsifier *1 1.5 weight parts
2. Ethylhexyl methoxysilicate *2 7.5 weight parts
3. Diethylamino hydroxybenzoyl hexyl benzoate *3 2.0 weight parts
4. Caprylyl methicone *4 2.0 weight parts
5. Isotridecyl isononanoate *5 3.0 weight parts
6. Isohexadecane 8.0 weight parts
7. Silicone film-forming agent *6 1.0 weight part
8. Disteardimonium hectorite *7 1.0 wt.
Phase B
9. Fine particulate titanium oxide *8 6.0 weight parts
10. Silicone dispersant *9 1.5 weight parts
11. Isohexadecane 7.5 weight parts
Phase C
12. Butylene glycol (BG) 7.0 weight parts
13. Sodium citrate 0.2 weight parts
14. Sodium chloride 0.5 weight parts
15. Water: remainder
Phase D
16. Silicone resin coated silicone elastomer particles of the examples 3.0 weight parts

*1 ES-5300 Formulation Aid manufactured by Dow Corning Toray Co., Ltd.
*2 Uvinyl MC80N manufactured by BASF
*3 Ubinal A Plus manufactured by BASF
*4 FZ-3196 manufactured by Dow Corning Toray Co., Ltd.
*5 Emarex INTD-139 manufactured by Nihon Emulsion Co., Ltd.
*6 FA-40021D Silicone Acrylate manufactured by Dow Corning Toray Co., Ltd.

*7 Benton 38V manufactured by Elementis
*8 MTY-02 manufactured by Tayca Co., Ltd.
*9 ES-5600 Silicone Glycerol Emulsifier manufactured by Dow Corning Toray Co., Ltd.

(Method of Preparation)
1. Mix phase A.
2. Mix phase B.
3. Mix phase C.
4. Mix phase A and phase B.
5. Add phase C slowly while stirring phase AB.
6. Add phase D and stir until uniform.

Formulation Example 11: O/W Sunscreen (Component)
Phase A
1. Polysorbate 80 *1 1.0 weight part
2. Mineral oil *2 10 weight parts
2. Triethylhexanoin 5.0 weight parts
3. Diethylamino hydroxybenzoyl hexyl benzoate *3 2.5 weight parts
4. Ethylhexyl methoxysilicate *4 7.5 weight parts
5. Caprylyl methicone *5 10 weight parts
6. Silicone resin coated silicone elastomer particles of the examples 5.0 weight parts
7. Titanium oxide dispersion *6 10 weight parts
Phase B
8. Carbomer 2% aqueous solution *7 15 weight parts
9. Water: remainder
10. 1% aqueous sodium hydroxide solution q.s.
11. Butylene glycol (BG) 5.0 weight parts
12. Glycerin 2.0 weight parts
*1 Reodor TW-0120V manufactured by Kao Corporation
*2 Hycor K-230 manufactured by Kaneda Co., Ltd.
*3 Ubinal A Plus manufactured by BASF
*4 Uvinyl MC80N manufactured by BASF
*5 FZ-3196 manufactured by Dow Corning Toray Co., Ltd.
*6 MTY-02 40 wt %, cyclopentasiloxane 50 wt %, ES-5600 Silicone Glycerol Emulsifier 10 wt % manufactured by Tayca Co., Ltd.
*7 Carbopol 980 manufactured by Lubrizol Corporation
(Method of Preparation)
Mix phase A.
Mix phase B.
Slowly add phase A while stirring phase B.

Formulation Example 12: Sheet-Type Toner (Component)
Phase A
1. (Acrylate/alkyl acrylate (C10-30)) cross polymer *1 0.1 weight parts
2. Water: remainder
3. Sodium hydroxide q.s.
Phase B
4. Glycerin 4.0 weight parts
5. Silicone resin coated silicone elastomer particles of the examples 2.0 weight parts
6. Aloe vera water 0.6 weight parts
7. Panthenol 0.3 weight parts
8. Water 5.0 weight parts
Phase C
9. Alkyl benzoate (C12-15) 2.7 weight parts
10. Polysorbate 20 *2 0.5 weight parts
11. Silicone cross-linked gel *3 3.5 weight parts
12. Cyclopentasiloxane *4 5.8 weight parts
13. Preservatives q.s.
14. Flavoring q.s.
*1 Carbopol ETD2020 manufactured by Lubrizol Corporation
*2 Tween 20 manufactured by Croda International
*3 9041 Silicone Elastomer Blend manufactured by Dow Corning Toray Co., Ltd.
*4 SH245 oil manufactured by Dow Corning Toray Co., Ltd.
(Method of Preparation)
Mix phase A.
Add phase B while stirring phase A.
Add phase C while vigorously stirring phase AB.
The emulsion described above is impregnated into a nonwoven fabric.

Formulation Example 13: Makeup Base (Component)
Phase A
1. Titanium oxide *1 3.0 weight parts
2. Mica 10 weight parts
3. Styrene/acrylate copolymer *2 3.0 weight parts
4. Pearl pigment *3 2.0 weight parts
5. Silicone resin coated silicone elastomer particles of an examples 25 weight parts
6. Talc 25 weight parts
Phase B
7. Silicone film-forming agent *4 5.0 weight parts
8. Ethylhexyl methoxysilicate 5.0 weight parts
9. Octocrylene 2.0 weight parts
10. Dimethicone *5 6.0 weight parts
11. Preservatives q.s.
12. Flavoring q.s.
Phase C
13. Silylated silica *6 4.0 weight parts
Phase D
14. Water: remainder
15. Propylene glycol 2.0 weight parts
16. PEG-32 3.0 weight parts
*1 SI Titanium CR-50 manufactured by Miyoshi Kasei, Inc.
*2 SunSpheres™ Powdet manufactured by Dow Inc.
*3 Timiron Glam Silver manufactured by Merck
*4 SH200 2cs manufactured by Dow Corning Toray Co., Ltd.
*5 FC50021D Resin Gum manufactured by Dow Corning Toray Co., Ltd.
*6 VM-2270 Aerogel Fine Particles manufactured by Dow Corning Toray Co., Ltd.
(Method of Preparation)
Mix phase A.
Mix phase B.
Mix phase A and phase B (AB phase).
Mix phase D.
Mix phase C and phase D (CD phase).
Mix the AB and CD phases described above.

Formulation Example 14: Mousse-Like Blush (Component)
Phase A
Vaseline 10 weight parts
Microcrystalline wax 5.0 weight parts
Silicone wax *1 4.0 weight parts
Phenyl trimethicone *2 8.0 weight parts Phase B
Titanium oxide *3 3.0 weight parts
Silicone resin coated silicone elastomer particles of the examples 8.0 weight parts
Silylated silica *4 0.5 weight parts
Silicone dispersant *5 1.0 weight part
Carmine 5.5 weight parts
   10. Titanium oxide *6 10 weight parts
Phase C
   11. Silicone film-forming agent *7 10 weight parts
   12. Silicone crosslinked product gel *8 10 weight parts
Phase D
   13. Caprylyl methicone *9 5.0 weight parts
   14. Dimethicone *10 10 weight parts
   15. Flavoring q.s.
   16. Preservatives q.s.
   *1 580 wax manufactured by Dow Corning Toray Co., Ltd.
   *2 SH556 manufactured by Dow Corning Toray Co., Ltd.
   *3 Eusolex T-S manufactured by Merck
   *4 VM-2270 Aerogel Fine Particles manufactured by Dow Corning Toray Co., Ltd.
   *5 ES-5300 Formulation Aid manufactured by Dow Corning Toray Co., Ltd.
   *6 SI Titanium CR-50 manufactured by Miyoshi Kasei, Inc.
   *7 FC50021D Resin Gum manufactured by Dow Corning Toray Co., Ltd.
   *8 EL-7040 Hydro Elastomer Blend manufactured by Dow Corning Toray Co., Ltd.
   *9 FZ-3196 manufactured by Dow Corning Toray Co., Ltd.
   *10 SH200 2cs manufactured by Dow Corning Toray Co., Ltd.

(Method of Preparation)
Heat phase A to 75° C.
Mix phase B.
Mix phase C.
Add phase C to phase B and heat to 75° C. (BC phase)
Add phase A little by little while stirring phase BC. (ABC phase)
Add phase D (mixture) to phase ABC and stir until uniform.

Formulation Example 15: Eyeshadow (Component)
Phase A
Silicone resin coated silicone elastomer particles of the examples 5.0 weight parts
Barium sulfate 6.0 weight parts
Zinc stearate 0.2 weight parts
Talc 62.6 weight parts
Basic Mg carbonate *1 1.2 weight parts
Titanium oxide *2 1.8 weight parts
Preservatives q.s.
Phase B
Red No. 7 15 weight parts
Phase C
Octyldodecyl myristate 2.0 weight parts
PEG-6 triisostearate*2 1.0 weight part
Stearic acid 2.0 weight parts
Silicone crosslinked product gel *3 1.5 weight parts
Silicone film-forming agent *4 1.5 weight parts
   *1 Basic Mg carbonate manufactured by Merck
   *2 SI Titanium CR-50 manufactured by Miyoshi Kasei, Inc.
   *3 9041 Silicone Elastomer Blend manufactured by Dow Corning Toray Co., Ltd.
   *4 FC50021D Resin Gum manufactured by Dow Corning Toray Co., Ltd.

(Method of Preparation)
Mix phase A.
Add phase B to phase A and stir. (AB phase)
Heat phase C to 75° C., add it to phase AB, and stir until uniform.
Transfer to a container and compress.

[Aqueous Suspension of Silicone Elastomer Particles Containing Oil Agents]

In the following formulation examples 16 to 18, the uniform aqueous suspension of the silicone resin coated silicone elastomer particles of the respective examples obtained in the manufacturing process of the above Examples 1 to 6 was used as-is as a cosmetic raw material without removing the water.

Formulation Example 16: O/W Base Cream (Component)
Phase A
Silicone emulsifier premix *1 3.0 weight parts
Silicone crosslinked product gel *2 25 weight parts
Dimethicone *3 2.0 weight parts
Phenyl trimethicone *4 2.0 weight parts
Tri(caprylic/capric) glyceryl 3.0 weight parts
Squalane 5.0 weight parts
Jojoba oil 3.0 weight parts
Pearl pigment *5 2.0 weight parts
Phase B
Water: remainder
   10. Glycerin 5.0 weight parts
   11. Preservatives q.s.
   12. Aqueous suspension of the silicone resin coated silicone elastomer particles of the examples 5.0 weight parts
   13. 1% sodium hyaluronate aqueous solution 10 weight parts
   *1 RM 2051 Thickening Agent manufactured by Dow Corning Toray Co., Ltd.
   *2 9041 Silicone Elastomer Blend manufactured by Dow Corning Toray Co., Ltd.
   *3 SH200C 6cs manufactured by Dow Corning Toray Co., Ltd.
   *4: SH556 manufactured by Dow Corning Toray Co., Ltd.
   *5 TIMIRON SPLENDID RED manufactured by Merck (Method of Preparation)
Mix phase A.
Mix phase B.
Slowly add phase B while stirring phase A.

Formulation Example 17: O/W Skin Cream (Component)
Phase A
   1. Stearic acid 1.0 weight part
   2. Polysorbate 80 1.2 weight parts
   3. Sorbitan sesquioleate 0.5 weight parts
   4. Glyceryl stearate 1.5 weight parts
   5. Cetearyl alcohol 1.5 weight parts
   6. Dimethicone *1 5.0 weight parts
   7. Squalane 5.0 weight parts
   8. Isotridecyl isononanoate 5.0 weight parts
   9. Tri(caprylic/capric acid) glyceryl 5.0 weight parts Phase B
- 10. Water: remainder
- 11. Butylene glycol (BG) 8.0 weight parts
- 12. Sodium hydroxide q.s.

Phase C
- 13. Carbomer *2 0.12 weight parts
- 14. Water 10 weight parts

Phase D
- 15. Aqueous suspension of the silicone resin coated silicone elastomer particles of the examples 7.0 weight parts

*1 SH200C 6cs manufactured by Dow Corning Toray Co., Ltd.
*2 Carbopol 980 manufactured by Lubrizol Corporation (Method of Preparation)

Heat phase A to 70° C.
Heat phase B to 70° C.
Slowly add phase B while stirring phase A. (AB phase)
Add phase C and phase D to phase AB, stir until uniform, and cool to room temperature.

Formulation Example 18: O/W All-in-One Gel (Component)

Phase A
1. Silicone emulsifier *1 0.5 weight parts
2. Dimethicone *2 1.0 weight part
3. Jojoba oil 1.0 weight part
4. Cyclopentasiloxane *3 2.0 weight parts Phase B
5. Water: remainder
6. Glycerin 10 weight parts
7. (Acrylate/alkyl acrylate (C10-30)) cross polymer *4 0.2 weight parts
8. Triethanolamine (TEA) q.s.
9. Preservatives q.s.
10. Aqueous suspension of the silicone resin coated silicone elastomer particles of the examples 5.0 weight parts

*1 ES-5373 Formulation Aid manufactured by Dow Corning Toray Co., Ltd.
*2 SH200C 6cs manufactured by Dow Corning Toray Co., Ltd.
*3 SH245 oil manufactured by Dow Corning Toray Co., Ltd.
*4 Carbopol Ultez20 Polymer manufactured by Lubrizol Corporation (Method of Preparation)

Mix phase A.
Mix phase B.
Slowly add phase A while stirring phase B.

Formulation Example 19: Liquid Lip (Component)

Phase A
Silylated silica *1 1.5 weight parts
Hydrogenated polyisobutene *2 10 weight parts Phase B
Silicone resin wax *3 3.0 weight parts
Beeswax 4.5 weight parts
Preservatives q.s.

Phase C
Titanium oxide *4 7.7 weight parts
Red No. 201 lake *5 2.75 weight parts
Red No. 202 *6 2.75 weight parts Phase D
Caprylyl methicone *7 10 weight parts
Silicone dispersant *8 2.0 weight parts Phase E
11. Barium sulfate 0.2 weight parts
12. Silicone resin coated silicone elastomer particles of the examples 2.0 weight parts Phase F
13. Clay mineral *9 7.0 weight parts
14. Antioxidants q.s.
15. Isododecane 15 weight parts
16. Dimethicone *10 10 weight parts
17. Silicone film-forming agent *11 20 weight parts
18. Ethylene/octene copolymer *12 0.5 weight part
19. Flavoring q.s.

*1 VM-2270 Aerogel Fine Particles manufactured by Dow Corning Toray Co., Ltd.
*2 Pearl Ream 4 manufactured by NOF Corporation
*3 SW-8005 C30 Resin Wax manufactured by Dow Corning Toray Co., Ltd.
*4 Unipure White LC 987 AS-EM manufactured by Sensient
*5 Unipure Red LC 304 manufactured by Sensient
*6 Unipure Red LC 3079 manufactured by Sensient
*7 SS-3408 manufactured by Dow Corning Toray Co., Ltd.
*8 ES-5300 Formulation Aid manufactured by Dow Corning Toray Co., Ltd.
*9 Bentone Gel(R) ISDV manufactured by Elementis
*10 SH200 1.5cs manufactured by Dow Corning Toray Co., Ltd.
*11 749 Fluid manufactured by Dow Corning Toray Co., Ltd.
*12 EcoSmooth™ Delight H manufactured by The Dow Chemical Company (Method of Preparation)

Mix phase A.
Phase B is heated to 80° C. to dissolve, then cooled to 60° C. and then phase A is added and stirred. (AB phase)
Stir phase C until uniform.
Mix phase C and phase D. (Phase CD)
Add phase CD to phase AB above and stir at 60° C. (Phase ABCD)
Add phase E to phase ABCD and stir. (Phase ABCDE)
Add phase F to phase ABCDE above, stir, and cool to 40° C. or below.

Formulation Example 20: Face Powder (Component)

Phase A
Talc*1 75 weight parts
Sericite*2 10 weight parts
Zinc oxide *3 5.0 weight parts
Mg stearate 4.0 weight parts
Silicone resin coated silicone elastomer particles of the examples 5.0 weight parts Phase B
6. Squalane 1.0 weight part

*1 SI talc manufactured by Miyoshi Chemical Co.
*2 SI Sericite FSE manufactured by Miyoshi Chemical Co.
*3 FINEX-30-OTS manufactured by Sakai Chemical Industry Co., Ltd.

(Method of Preparation)

Mix phase A.
Add phase B to phase A and stir until uniform.

Formulation Example 21. Hair chalk (Composition) Phase A
Talc 63.7 weight parts
Mg stearate 3.0 weight parts
Methyl paraben 0.2 weight parts
Propylparaben 0.1 weight parts
Silicone resin coated silicone elastomer particles of the examples 5.0 weight parts
Titanium oxide *1 5.0 weight parts
Phase B
7. Red No. 202 *2 15 weight parts
Phase C
Silicone crosslinked product gel* 3 8.0 weight parts
*1 Unipure White LC 987 AS-EM manufactured by Sensient
*2 Unipure Red LC 3079 manufactured by Sensient
*3 9041 Silicone Elastomer Blend manufactured by Dow Corning Toray Co., Ltd.
(Method of Preparation)
Mix phase A.
Add phase B and mix.
Add phase C and mix.
Transfer to a container and compress.

INDUSTRIAL APPLICABILITY

The silicone resin coated silicone elastomer particles of the present invention have superior storage stability, workability, and compounding stability because aggregation over time is suppressed, and they have excellent uniform dispersibility in organic resins and oil-based raw material and are useful as an organic resin additive for the curable organic resins described above (semiconductor materials, paints and coatings, and the like). Furthermore, the silicone resin coated silicone elastomer particles of the present invention can be used in skin cosmetic composition products, make-up cosmetics, and the like since they can improve the tactile sensation of cosmetics when blended in cosmetics as cosmetic raw materials. In addition, taking advantage of the physical properties thereof, the silicone resin coated silicone elastomer particles of the present invention can be used as an additive for thermosetting resin compositions, thermoplastic resin compositions, and the like, or as a surface lubricant for plastic films, as application to electronic materials.

The invention claimed is:

1. A silicone resin coated silicone elastomer particle, wherein part or all of the surface thereof is coated with a DQ silicone resin comprising only a condensation reaction product of a diorganodialkoxysilane and a tetraalkoxysilane,
the DQ silicone resin comprising D siloxane units represented by $R^1_2SiO_{2/2}$ and a Q siloxane unit represented by $SiO_{4/2}$ where $R^1$ is an alkyl group having 1 to 20 carbon atoms or an aryl group having 6 to 20 carbon atoms; and
is provided with a structure in which at least two silicon atoms in the silicone elastomer particle are crosslinked by a silalkylene group having a carbon number of 2 to 20;
wherein the silicone elastomer particles prior to curing and coating with the DQ silicone resin are formed from a crosslinkable composition comprising:
(a) an organopolysiloxane having at least two alkenyl groups with 2 to 20 carbon atoms in the molecule;
(b) an organohydrogenpolysiloxane having at least two silicon-bonded hydrogen atoms in the molecule; and
(c) a hydrosilylation reaction catalyst;
wherein the molar ratio of the alkenyl group content (Alk) of component (a) to the silicon-bonded hydrogen atom content (H) of component (b) is in the range of 0.7 to 1.5 (H/Alk);
wherein the content of silicon-bonded hydrogen per unit mass is 300 ppm or less; and
wherein each D siloxane unit of the DQ silicone resin is provided by the diorganodialkoxysilane, each Q siloxane unit is provided by the tetraalkoxysilane, and the condensation reaction product has a weight ratio of from 8:2 to 3:7 D to Q siloxane units (D:Q).

2. The silicone resin coated silicone elastomer particle according to claim 1, wherein the DQ silicone resin coating amount is in the range of 5.0 to 40.0 mass parts for 100 mass parts of the silicone elastomer particles.

3. The silicone resin coated silicone elastomer particle according to claim 1, wherein the weight ratio of D to Q siloxane units is in the range of 7:3 to 5:5 (D:Q).

4. The silicone resin coated silicone elastomer particle according to claim 1, wherein the average primary particle diameter of the silicone elastomer particle as measured by a laser diffraction scattering method is 0.5 to 20 μm.

5. The silicone resin coated silicone elastomer particle according to claim 1, wherein the silicone elastomer particle in a state not coated with a silicone resin has a JIS-A hardness, as measured by curing the pre-cure crosslinkable composition for forming the silicone elastomer particle in sheet form, in the range of 10 to 80.

6. The silicone resin coated silicone elastomer particle according to claim 1, wherein the diorganodialkoxysilane is dimethyldimethoxysilane or diphenyldimethoxysin, and the tetraalkoxysilane is tetraethoxysilane.

7. The silicone resin coated silicone elastomer particle according to claim 1, wherein the DQ silicone resin coating on the surface of the silicone elastomer particle is a uniform and smooth film.

8. The silicone resin coated silicone elastomer particle according to claim 1, wherein the content of silicon-bonded hydrogen per unit mass is 150 ppm or less.

9. An organic resin additive comprising the silicone resin coated silicone elastomer particle according to claim 1.

10. An organic resin comprising the silicone resin coated silicone elastomer particle according to claim 1.

11. A curable organic resin composition comprising the silicone resin coated silicone elastomer particle according to claim 1.

12. A paint composition or coating composition comprising the silicone resin coated silicone elastomer particle according to claim 1.

13. A cosmetic composition comprising the silicone resin coated silicone elastomer particle according to claim 1.

14. The silicone resin coated silicone elastomer particle according to claim 1, wherein the silicone resin coating thereof consists of the DQ silicone resin, and the DQ silicone resin consists of the condensation reaction product of the diorganodialkoxysilane and the tetraalkoxysilane.

* * * * *